US010117597B2

(12) United States Patent
Beckers et al.

(10) Patent No.: US 10,117,597 B2
(45) Date of Patent: Nov. 6, 2018

(54) APPARATUS, METHODS AND ARTICLES FOR FOUR DIMENSIONAL (4D) FLOW MAGNETIC RESONANCE IMAGING USING COHERENCY IDENTIFICATION FOR MAGNETIC RESONANCE IMAGING FLOW DATA

(71) Applicant: ARTERYS INC., San Francisco, CA (US)

(72) Inventors: Fabien Beckers, San Francisco, CA (US); Albert Hsiao, Menlo Park, CA (US); John Axerio-Cilies, San Francisco, CA (US); Torin Arni Taerum, Calgary (CA); Daniel Marc Raymond Beauchamp, Toronto (CA)

(73) Assignee: ARTERYS INC., San Francisco, CA (US)

( * ) Notice: Subject to any disclaimer, the term of this patent is extended or adjusted under 35 U.S.C. 154(b) by 29 days.

(21) Appl. No.: 15/112,130

(22) PCT Filed: Jan. 16, 2015

(86) PCT No.: PCT/US2015/011851
§ 371 (c)(1),
(2) Date: Jul. 15, 2016

(87) PCT Pub. No.: WO2015/109254
PCT Pub. Date: Jul. 23, 2015

(65) Prior Publication Data
US 2016/0338613 A1 Nov. 24, 2016

Related U.S. Application Data
(60) Provisional application No. 61/928,702, filed on Jan. 17, 2014.

(51) Int. Cl.
G06K 9/00 (2006.01)
A61B 5/055 (2006.01)
(Continued)

(52) U.S. Cl.
CPC ............ A61B 5/055 (2013.01); A61B 5/0044 (2013.01); A61B 5/021 (2013.01);
(Continued)

(58) Field of Classification Search
None
See application file for complete search history.

(56) References Cited

U.S. PATENT DOCUMENTS 5,115,812 A 5/1992 Sano et al.
6,934,698 B2 8/2005 Judd et al.
(Continued)

FOREIGN PATENT DOCUMENTS

JP 2-147048 A 6/1990
JP 5-84231 A 4/1993
(Continued)

OTHER PUBLICATIONS

Japanese Office Action, dated Aug. 24, 2017, for Japanese Application No. 2016-175588, 8 pages. (with English Translation).
(Continued)

Primary Examiner — Idowu O Osifade
(74) Attorney, Agent, or Firm — Seed IP Law Group LLP

(57) ABSTRACT

An MRI image processing and analysis system may identify instances of structure in MRI flow data, e.g., coherency, derive contours and/or clinical markers based on the identified structures. The system may be remotely located from one or more MRI acquisition systems, and perform: perform error detection and/or correction on MRI data sets (e.g., phase error correction, phase aliasing, signal unwrapping, and/or on other artifacts); segmentation; visualization of
(Continued)

flow (e.g., velocity, arterial versus venous flow, shunts) superimposed on anatomical structure, quantification; verification; and/or generation of patient specific 4-D flow protocols. An asynchronous command and imaging pipeline allows remote image processing and analysis in a timely and secure manner even with complicated or large 4-D flow MRI data sets.

40 Claims, 10 Drawing Sheets

(51) Int. Cl.
| | |
|---|---|
| A61B 5/00 | (2006.01) |
| A61B 5/02 | (2006.01) |
| A61B 5/026 | (2006.01) |
| G06F 19/00 | (2018.01) |
| G01R 33/563 | (2006.01) |
| G01R 33/565 | (2006.01) |
| A61B 5/021 | (2006.01) |
| G06T 7/12 | (2017.01) |
| G06T 7/168 | (2017.01) |
| G06T 7/174 | (2017.01) |
| A61B 5/08 | (2006.01) |
| G01R 33/56 | (2006.01) |

(52) U.S. Cl.
CPC ...... *A61B 5/02007* (2013.01); *A61B 5/02014* (2013.01); *A61B 5/0263* (2013.01); *A61B 5/7257* (2013.01); *G01R 33/56308* (2013.01); *G01R 33/56545* (2013.01); *G06F 19/321* (2013.01); *G06T 7/12* (2017.01); *G06T 7/168* (2017.01); *G06T 7/174* (2017.01); *A61B 5/08* (2013.01); *A61B 2576/023* (2013.01); *G01R 33/5608* (2013.01); *G06T 2207/10088* (2013.01); *G06T 2207/20056* (2013.01); *G06T 2207/20076* (2013.01); *G06T 2207/30048* (2013.01); *G06T 2207/30104* (2013.01)

(56) References Cited

U.S. PATENT DOCUMENTS

| | | | |
|---|---|---|---|
| 7,139,417 | B2 | 11/2006 | Nicolas et al. |
| 7,254,436 | B2 | 8/2007 | Judd et al. |
| 7,457,656 | B2 | 11/2008 | Judd et al. |
| 7,668,835 | B2 | 2/2010 | Judd et al. |
| 7,958,100 | B2 | 6/2011 | Judd et al. |
| 8,055,636 | B2 | 11/2011 | Judd et al. |
| 8,166,381 | B2 | 4/2012 | Judd et al. |
| 8,837,800 | B1 | 9/2014 | Bammer et al. |
| 9,165,360 | B1 | 10/2015 | Bates et al. |
| 9,430,828 | B2 | 8/2016 | Wu et al. |
| 9,513,357 | B2 | 12/2016 | Hsiao et al. |
| 2002/0146159 | A1 | 10/2002 | Nolte |
| 2003/0234781 | A1 | 12/2003 | Laidlaw et al. |
| 2005/0238233 | A1 | 10/2005 | Mulet Parada et al. |
| 2006/0106877 | A1 | 5/2006 | Lee |
| 2006/0155187 | A1 | 7/2006 | Zhao et al. |
| 2007/0061460 | A1 | 3/2007 | Khan et al. |
| 2008/0054900 | A1 | 3/2008 | Polzin |
| 2009/0226064 | A1 | 9/2009 | El Fakhri et al. |
| 2010/0085052 | A1 | 4/2010 | Johnson et al. |
| 2010/0094122 | A1 | 4/2010 | Kiraly |
| 2010/0145194 | A1 | 6/2010 | Joshi et al. |
| 2010/0280352 | A1 | 11/2010 | Ionasec et al. |
| 2011/0064294 | A1 | 3/2011 | Abe et al. |
| 2011/0230756 | A1 | 9/2011 | Axel Odeen et al. |
| 2011/0311120 | A1 | 12/2011 | Maizeroi-Eugene |
| 2012/0076380 | A1 | 3/2012 | Gühring et al. |
| 2012/0114205 | A1 | 5/2012 | Tang et al. |
| 2012/0184840 | A1 | 7/2012 | Najarian et al. |
| 2012/0271156 | A1 | 10/2012 | Bi et al. |
| 2013/0066229 | A1 | 3/2013 | Wolff |
| 2013/0259351 | A1 | 10/2013 | Wiemker, II |
| 2014/0086465 | A1 | 3/2014 | Wu et al. |
| 2015/0238148 | A1 | 8/2015 | Georgescu et al. |
| 2015/0324690 | A1 | 11/2015 | Chilimbi et al. |
| 2015/0374237 | A1* | 12/2015 | Hu .......................... A61B 5/055 600/413 |
| 2017/0045600 | A1 | 2/2017 | Hsiao et al. |
| 2017/0046616 | A1 | 2/2017 | Socher et al. |

FOREIGN PATENT DOCUMENTS

| | | |
|---|---|---|
| JP | 8-38444 A | 2/1996 |
| JP | 8-140960 A | 6/1996 |
| JP | 2008-526382 A | 7/2008 |
| JP | 2009-261519 A | 11/2009 |
| JP | 2010-82321 A | 4/2010 |
| WO | 00/67185 A1 | 11/2000 |
| WO | 2009/142167 A1 | 11/2009 |
| WO | 2010/038138 A1 | 4/2010 |
| WO | 2012/018560 A2 | 2/2012 |
| WO | 2013/006709 A2 | 1/2013 |
| WO | 2015/031641 A1 | 3/2015 |
| WO | 2017/091833 A1 | 6/2017 |
| WO | 2017/106645 A1 | 6/2017 |

OTHER PUBLICATIONS

Abadi et al., "TensorFlow: Large-Scale Machine Learning on Heterogeneous Distributed Systems," *The Computing Research Repository 1603.04467*, 2016. (19 pages).
Avendi et al., A combined deep-learning and deformable-model approach to fully automatic segmentation of the left ventricle in cardiac MRI, *Medical Image Analysis 30*:108-119, 2016. (34 pages).
Bergstra et al., "Random Search for Hyper-Parameter Optimization," *Journal of Machine Learning Research 13*(Feb):281-305, 2012.
Chen et al., "Automatic Detection of Cerebral Microbleeds via Deep Learning Based 3D Feature Representation," *IEEE 12th International Symposium on Biomedical Imaging*, New York City, New York, USA, Apr. 16-19, 2015, pp. 764-767.
Chernobelsky et al., "Baseline Correction of Phase Contrast Images Improves Quantification of Blood Flow in the Great Vessels," *Journal of Cardiovascular Magnetic Resonance 9*(4):681-685, 2007.
Chinese Office Action, dated Aug. 24, 2015, for Chinese Application No. 201280042949.7, 21 pages. (with English Translation).
Chinese Office Action, dated Jan. 21, 2016, for Chinese Application No. 201280042949.7, 8 pages. (with English Translation).
Dong et al., "Image Super-Resolution Using Deep Convolutional Networks," *IEEE Transactions on Pattern Analysis and Machine Intelligence 38*(2):295-307, 2016. (14 pages).
Extended European Search Report, dated Jul. 14, 2017, for European Application No. 15737417.4-1657, 8 pages.
Extended European Search Report, dated Jul. 7, 2015, for European Application No. 12807483.8-1560, 11 pages.
Firmino et al., "Computer-aided detection (CADe) and diagnosis (CADx) system for lung cancer with likelihood of malignancy," *BioMedical Engineering OnLine 15*:2, 2016. (17 pages).
Gatehouse et al., "Flow measurement by cardiovascular magnetic resonance: a multi-centre multi-vendor study of background phase offset errors that can compromise the accuracy of derived regurgitant or shunt flow measurements," *Journal of Cardiovascular Magnetic Resonance 12*:5, 2010. (8 pages).
Golden et al., "Automated Cardiac Volume Segmentation," U.S. Appl. No. 62/415,666, filed Nov. 1, 2016, 119 pages.
Golden et al., "Automated Segmentation Utilizing Fully Convolutional Networks," U.S. Appl. No. 62/451,482, filed Jan. 27, 2017, 113 pages.
He et al., "Deep Residual Learning for Image Recognition," *IEEE Conference on Computer Vision and Pattern Recognition*, Las Vegas, Nevada, USA, Jun. 27-30, 2016, pp. 770-778.

(56) References Cited

OTHER PUBLICATIONS

He et al., "Identity Mappings in Deep Residual Networks," 14th European Conference on Computer Vision, Amsterdam, The Netherlands, Oct. 8-16, 2016, 15 pages.

Hsiao et al., "Evaluation of Valvular Insufficiency and Shunts with Parallel-imaging Compressed-sensing 4D Phase-contrast MR Imaging with Stereoscopic 3D Velocity-fusion Volume-rendered Visualization," Radiology 265(1):87-95, 2012.

Hsiao et al., "Rapid Pediatric Cardiac Assessment of Flow and Ventricular Volume With Compressed Sensing Parallel Imaging Volumetric Cine Phase-Contrast MRI," American Journal of Roentgenology 198(3):W250-W259, 2012.

International Preliminary Report on Patentability, dated Jan. 7, 2014, for International Application No. PCT/US2012/045575, 6 pages.

International Preliminary Report on Patentability, dated Jul. 19, 2016, for International Application No. PCT/US2015/011851, 13 pages.

International Search Report and Written Opinion, dated Mar. 13, 2017, for International Application No. PCT/US2016/064028, 15 pages.

Japanese Office Action, dated Apr. 12, 2016, for Japanese Application No. 2014-519295, 6 pages. (with English Translation).

Kass et al., "Snakes: Active Contour Models," International Journal of Computer Vision 1(4):321-331, 1988.

Kilner et al., "Flow Measurement by Magnetic Resonance: A Unique Asset Worth Optimising," Journal of Cardiovascular Magnetic Resonance 9(4):723-728, 2007.

Kingma et al., "Adam: A Method for Stochastic Optimization," 3rd International Conference for Learning Representations, San Diego, California, USA, May 7-9, 2015, 15 pages.

Kuhn, "The Hungarian Method for the Assignment Problem," Naval Research Logistics Quarterly 2(1-2):83-97, 1955. (16 pages).

Lau et al., "DeepVentricle: Automated Cardiac MRI Ventricle Segmentation with Deep Learning," Conference on Machine Intelligence in Medical Imaging, Alexandria, Virginia, USA, Sep. 12-13, 2016, 5 pages.

Lieman-Sifry et al., "Automated Lesion Detection, Segmentation, and Longitudinal Identification,"0 U.S. Appl. No. 62/512,610, filed May 30, 2017, 87 pages.

Long et al., "Fully convolutional networks for semantic segmentation," IEEE Conference on Computer Vision and Pattern Recognition, Boston, Massachusetts, USA, Jun. 7-12, 2015, pp. 3431-3440.

Maier et al., "Classifiers for Ischemic Stroke Lesion Segmentation: A Comparison Study," PLoS One 10(12):e0145118, 2015. (16 pages).

Mordvintsev et al., "Inceptionism: Going Deeper into Neural Networks," Jun. 17, 2015, URL=http://googleresearch.blogspot.co.uk/2015/06/inceptionism-going-deeper-into-neural.html, download date Jul. 18, 2017, 8 pages.

Noh et al., "Learning Deconvolution Network for Semantic Segmentation," IEEE International Conference on Computer Vision, Santiago, Chile, Dec. 7-13, 2015, pp. 1520-1528.

Notice of Allowance, dated Aug. 4, 2016, for U.S. Appl. No. 14/118,964, Hsiao et al., "Comprehensive Cardiovascular Analysis With Volumetric Phase-Contrast MRI," 8 pages.

Paszke et al., "ENet: A Deep Neural Network Architecture for Real-Time Semantic Segmentation," The Computing Research Repository 1606.02147, 2016. (10 pages).

Payer et al., "Regressing Heatmaps for Multiple Landmark Localization using CNNs," 19th International Conference on Medical Image Computing and Computer-Assisted Intervention, Athens, Greece, Oct. 17-21, 2016, pp. 230-238. (8 pages).

Preliminary Amendment, filed Jan. 8, 2014, for U.S. Appl. No. 14/118,964, Hsiao et al., "Comprehensive Cardiovascular Analysis With Volumetric Phase-Contrast MRI," 16 pages.

Preliminary Amendment, filed Nov. 2, 2016, for U.S. Appl. No. 15/339,475, Hsiao et al., "Comprehensive Cardiovascular Analysis with Volumetric Phase-Contrast MRI," 8 pages.

Preliminary Amendment, filed Nov. 20, 2013, for U.S. Appl. No. 14/118,964, Hsiao et al., "Comprehensive Cardiovascular Analysis With Volumetric Phase-Contrast MRI," 3 pages.

Restriction Requirement, dated Sep. 9, 2015, for U.S. Appl. No. 14/118,964, Hsiao et al., "Comprehensive Cardiovascular Analysis with Volumetric Phase-Contrast MRI," 7 pages.

Ronneberger et al., "U-Net: Convolutional Networks for Biomedical Image Segmentation," 18th International Conference on Medical Image Computing and Computer-Assisted Intervention, Munich, Germany, Oct. 5-9, 2015, pp. 234-241.

Rosenfeld et al., "An Improved Method of Angle Detection on Digital Curves," IEEE Transactions on Computers C-24(9):940-941, 1975.

Schulz-Menger, "Standardized image interpretation and post processing in cardiovascular magnetic resonance: Society for Cardiovascular Magnetic Resonance (SCMR) Board of Trustees Task Force on Standardized Post Processing," Journal of Cardiovascular Magnetic Resonance 15:35, 2013. (19 pages).

Simard et al., "Best Practices for Convolutional Neural Networks Applied to Visual Document Analysis," 7th International Conference on Document Analysis and Recognition, Edinburgh, United Kingdom, Aug. 3-6, 2003, pp. 958-963.

Simpson et al., "Estimation of Coherence Between Blood Flow and Spontaneous EEG Activity in Neonates," IEEE Transactions on Biomedical Engineering 52(5):852-858, 2005.

Supplemental Amendment, filed Jun. 6, 2016, for U.S. Appl. No. 14/118,964, Hsiao et al., "Comprehensive Cardiovascular Analysis With Volumetric Phase-Contrast MRI," 21 pages.

Tran, "A Fully Convolutional Neural Network for Cardiac Segmentation in Short-Axis MRI," The Computing Research Repository 1604.00494, 2016. (21 pages).

Walker et al., "Semiautomated method for noise reduction and background phase error correction in MR phase velocity data," Journal of Magnetic Resonance Imaging 3(3):521-530, 1993.

Wong et al., "Segmentation of Myocardium Using Velocity Field Constrained Front Propagation," 6th IEEE Workshop on Applications of Computer Vision, Orlando, Florida, USA, Dec. 3-4, 2002, pp. 84-89.

Yu et al., "Multi-Scale Context Aggregation by Dilated Convolutions," International Conference on Learning Representations, San Juan, Puerto Rico, May 2-4, 2016, 13 pages.

Zhao et al., "Performance of computer-aided detection of pulmonary nodules in low-dose CT: comparison with double reading by nodule volume," European Radiology 22(10):2076-2084, 2012.

Zhu et al., "A geodesic-active-contour-based variational model for short-axis cardiac MR image segmentation," International Journal of Computer Mathematics 90(1):124-139, 2013. (18 pages).

Bock et al., "Optimized Pre-Processing of Time-Resolved 2D and 3D Phase Contrast MRI Data," Proc. Intl. Soc. Mag. Reson. Med. 15:3138, 2007.

Delles et al., "Quadratic Phase Offset Error Correction of Velocity-Encoded Magnetic Resonance Imaging Data," Int J Cars 4(Suppl 1): S10-S11, 2009.

Frydrychowicz et al., "Four-Dimensional Phase Contrast Magnetic Resonance Angiography: Potential Clinical Applications," Eur J Radiol. 80(1):24-35, Oct. 2011.

Giese et al., "Optimized Pre-Processing Strategy for the Correction of Gradient Field Inhomogeneities in 3D-PC-MRI," Proc. Intl. Soc. Mag. Reson. Med. 16:1371, 2008.

Hsiao et al., "Improved Cardiovascular Flow Quanfitication [sic] with Time-Resolved Volumetric Phase-Contrast MRI," Pediatr Radiol 41(6), 18 pages, Jun. 2011.

Hsiao et al., "Comprehensive Cardiovascular Analysis With Volumetric Phase-Contrast MRI," Office Action dated Oct. 20, 2015 for U.S. Appl. No. 14/118,964, 10 pages.

Hsiao et al., "Comprehensive Cardiovascular Analysis With Volumetric Phase-Contrast MRI," Amendment filed Oct. 20, 2015 for U.S. Appl. No. 14/118,964, 20 pages.

Hsiao et al., "Comprehensive Cardiovascular Analysis With Volumetric Phase-Contrast MRI," Office Action dated Mar. 3, 2016 for U.S. Appl. No. 14/118,964, 12 pages.

(56) References Cited

OTHER PUBLICATIONS

Hsiao et al., "Comprehensive Cardiovascular Analysis With Volumetric Phase-Contrast MRI," Amendment filed Jun. 6, 2016 for U.S. Appl. No. 14/118,964, 21 pages.
International Search Report, dated Jan. 14, 2013, for PCT/US2012/045575, 3 pages.
International Search Report, dated Jul. 17, 2015, for PCT/US2015/011851, 5 pages.
Lankhaar et al., "Correction of Phase Offset Errors in Main Pulmonary Artery Flow Quantification," *Journal of Magnetic Resonance Imaging* 22:73-79, 2005.
Markl et al., "Generalized Modeling of Gradient Field Non-Linearities and Reconstruction of Phase Contrast MRI Measurements," *Proc. Intl. Soc. Mag., Reson. Med.* 11:1027, 2003.
Markl et al., "Generalized Reconstruction of Phase Contrast MRI: Analysis and Correction of the Effect of Gradient Field Distortions," *Magnetic Resonance in Medicine* 50:791-801, 2003.
Peeters, et al., "Analysis and Correction of Gradient Nonlinearity and $B_0$ Inhomogeneity Related Scaling Errors in 2DPC Flow Measurements,"*Magn Reson Med* 53(1):126-133, 2005.
Written Opinion, dated Jan. 14, 2013, for PCT/US2012/045575, 5 pages.
Written Opinion, dated Jul. 17, 2015, for PCT/US2015/011851, 12 pages.
American College of Radiology, "Liver Reporting & Data System," URL=https://www.acr.org/Clinical-Resources/Reporting-and-Data-Systems/LI-RADS, download date Jun. 28, 2018, 4 pages.
American College of Radiology, "Lung CT Screening Reporting & Data System,"URL=https://www.acr.org/Clinical-Resources/Reporting-and-Data-Systems/Lung-Rads, download date Jun. 28, 2018, 4 pages.
Armato III et al., "The Lung Image Database Consortium (LIDC) and Image Database Resource Initiative (IDRI): A Completed Reference Database of Lung Nodules on CT Scans," *Medical Physics* 38(2):915-931, 2011.
Baur et al., "MelanoGANs: High Resolution Skin Lesion Synthesis with GANs," arXiv:1804.04338v1 [cs.CV], Apr. 12, 2018, 8 pages.
Berens et al., "ZNET—Lung Nodule Detection," Lung Nodule Analysis 2016, URL=https://luna16.grand-challenge.org/serve/public_html/.../ZNET_NDET_160831.pdf/, download date Jun. 28, 2018, 4 pages.
Bock et al., "4D Phase Contrast MRI at 3 T: Effect of Standard and Blood-Pool Contrast Agents on SNR, PC-MRA, and Blood Flow Visualization," *Magnetic Resonance in Medicine* 63(2):330-338, 2010.
Chung et al., "Malignancy estimation of Lung-RADS criteria for subsolid nodules on CT: accuracy of low and high risk spectrum when using NLST nodules," *European Radiology* 27(11):4672-4679, 2017.
Chuquicusma et al., "How to Fool Radiologists with Generative Adversarial Networks? A Visual Turing Test for Lung Cancer Diagnosis," arXiv:1710.09762v2 [cs.CV], Jan. 9, 2018, 5 pages.
Costa et al., "Towards Adversarial Retinal Image Synthesis," arXiv:1701.08974v1 [cs.CV], Jan. 31, 2017, 11 pages.
Díaz et al., "Fast Noncontinuous Path Phase-Unwrapping Algorithm Based on Gradients and Mask," *9th Iberoamerican Congress on Pattern Recognition*, Puebla, Mexico, Oct. 26-29, 2004, pp. 116-123.
Esteva et al., "Dermatologist-level classification of skin cancer with deep neural networks," *Nature* 542(7639):115-118, 2017. (12 pages).
European Office Action, dated May 29, 2018, for European Application No. 15737417.4-1115, 5 pages.
Fluckiger et al., "Left Atrial Flow Velocity Distribution and Flow Coherence Using Four-Dimensional Flow MRI: A Pilot Study Investigating the Impact of Age and Pre- and Postintervention Atrial Fibrillation on Atrial Hemodynamics," *Journal of Magnetic Resonance Imaging* 38(3):580-587, 2013.
Frid-Adar et al., "GAN-based Synthetic Medical Image Augmentation for increased CNN Performance in Liver Lesion Classification," arXiv:1803.01229v1 [cs.CV], Mar. 3, 2018, 10 pages.
Golden et al., "Content Based Image Retrieval for Lesion Analysis," U.S. Appl. No. 62/589,805, filed Nov. 22, 2017, 189 pages.
Golden et al., "Patient Outcomes Prediction System," U.S. Appl. No. 62/589,838, filed Nov. 22, 2017, 187 pages.
Goodfellow et al., "Generative Adversarial Nets," arXiv:1406.2661v1 [stat.ML], Jun. 10, 2014, 9 pages.
Gulshan et al., "Development and Validation of a Deep Learning Algorithm for Detection of Diabetic Retinopathy in Retinal Fundus Photographs," *Journal of the American Medical Association* 316(22):2402-2410, 2016.
Hennemuth et al., "Fast Interactive Exploration of 4D MRI Flow Data," *Proceedings of SPIE* 7964:79640E, 2011. (11 pages).
Hsiao et al., "An Integrated Visualization and Quantitative Analysis Platform for Volumetric Phase-Contrast MRI," U.S. Appl. No. 61/571,908, filed Jul. 7, 2011, 18 pages.
Huhdanpaa et al., "Image Coregistration: Quantitative Processing Framework for the Assessment of Brain Lesions," *Journal of Digital Imaging* 27(3):369-379, 2014.
International Preliminary Report on Patentability, dated Jun. 19, 2018, for International Application No. PCT/US2016/067170, 7 pages.
International Preliminary Report on Patentability, dated May 29, 2018, for International Application No. PCT/US2016/064028, 13 pages.
International Search Report and Written Opinion, dated Mar. 16, 2017, for International Application No. PCT/US2016/067170, 9 pages.
Isola et al., "Image-to-Image Translation with Conditional Adversarial Networks," arXiv:1611.07004v2 [cs.CV], Nov. 22, 2017, 17 pages.
Japanese Office Action, dated Mar. 13, 2018, for Japanese Application No. 2016-175588, 4 pages. (with English Translation).
Kainz et al., "In vivo interactive visualization of four-dimensional blood flow patterns," *The Visual Computer* 25(9):853-862, 2009.
Lau et al., "Simulating Abnormalities in Medical Images With Generative Adversarial Networks," U.S. Appl. No. 62/683,461, filed Jun. 11, 2018, 39 pages.
Law et al., "Automated Three Dimensional Lesion Segmentation," U.S. Appl. No. 62/589,876, filed Nov. 22, 2017, 182 pages.
Lecun et al., "Gradient-Based Learning Applied to Document Recognition," *Proceedings of the IEEE* 86(11):2278-2324, 1998.
Leibowitz et al., "Systems and Methods for Interaction With Medical Image Data," U.S. Appl. No. 62/589,872, filed Nov. 22, 2017, 187 pages.
Mao et al., "Least Squares Generative Adversarial Networks," arXiv:1611.04076v3 [cs.CV], Apr. 5, 2017, 16 pages.
Mariani et al., "BAGAN: Data Augmentation with Balancing GAN," arXiv:1803.09655v2 [cs.CV], Jun. 5, 2018, 9 pages.
Markl et al., "Comprehensive 4D velocity mapping of the heart and great vessels by cardiovascular magnetic resonance," *Journal of Cardiovascular Magnetic Resonance* 13(1):7, 2011. (22 pages).
Mirza et al., "Conditional Generative Adversarial Nets," arXiv:1411.1784v1 [cs.LG], Nov. 6, 2014, 7 pages.
Muja et al., "Fast Approximate Nearest Neighbors with Automatic Algorithm Configuration," *International Conference on Computer Vision Theory and Applications*, Lisboa, Portugal, Feb. 5-8, 2009, pp. 331-340.
National Lung Screening Trial Research Team, "Reduced Lung-Cancer Mortality with Low-Dose Computed Tomographic Screening," *The New England Journal of Medicine* 365(5):395-409, 2011.
Newton et al., "Three Dimensional Voxel Segmentation Tool," U.S. Appl. No. 62/589,772, filed Nov. 22, 2017, 180 pages.
Öberg, "Segmentation of cardiovascular tree in 4D from PC-MRI images," Master's Thesis, Lund University, Lund, Sweden, Apr. 8, 2013, 49 pages.
Odena et al., "Conditional Image Synthesis with Auxiliary Classifier GANs," arXiv:1610.09585v4 [stat.ML], Jul. 20, 2017, 12 pages.
Office Action, dated Apr. 23, 2018, for U.S. Appl. No. 15/339,475, Hsiao et al., "Comprehensive Cardiovascular Analysis With Volumetric Phase-Contrast MRI," 12 pages.
Plassard et al., "Revealing Latent Value of Clinically Acquired CTs of Traumatic Brain Injury Through Multi-Atlas Segmentation in a Retrospective Study of 1,003 with External Cross-Validation," *Proceedings of SPIE* 9413:94130K, 2015. (13 pages).

(56) References Cited

OTHER PUBLICATIONS

Radford et al., "Unsupervised Representation Learning with Deep Convolutional Generative Adversarial Networks," arXiv:1511.06434v2 [cs.LG], Jan. 7, 2016, 16 pages.

Russakovsky et al., "ImageNet Large Scale Visual Recognition Challenge," *International Journal of Computer Vision* 115(3):211-252, 2015.

Salehinejad et al., "Generalization of Deep Neural Networks for Chest Pathology Classification in X-Rays Using Generative Adversarial Networks," arXiv:1712.01636v2 [cs.CV], Feb. 12, 2018, 5 pages.

Shrivastava et al., "Learning from Simulated and Unsupervised Images through Adversarial Training," arXiv:1612.07828v2 [cs.CV], Jul. 19, 2017, 16 pages.

Sixt et al., "RenderGAN: Generating Realistic Labeled Data," arXiv:1611.01331v5 [cs.NE], Jan. 12, 2017, 15 pages.

Suzuki, "Pixel-Based Machine Learning in Medical Imaging," *International Journal of Biomedical Imaging* 2012:792079, 2012. (18 pages).

Taerum et al., "Automated Lesion Detection, Segmentation, and Longitudinal Identification," U.S. Appl. No. 62/589,825, filed Nov. 22, 2017, 192 pages.

Töger et al., "Vortex Ring Formation in the Left Ventricle of the Heart: Analysis by 4D Flow MRI and Lagrangian Coherent Structures," *Annals of Biomedical Engineering* 40(12):2652-2662, 2012.

Van Riel et al., "Observer Viability for Classification of Pulmonary Nodules on Low-Dose CT Images and Its Effect on Nodule Management," *Radiology* 277(3):863-871, 2015.

Wolterink et al., "Deep MR to CT Synthesis using Unpaired Data," arXiv:1708.01155v1 [cs.CV], Aug. 3, 2017, 10 pages.

Yuh et al., "Interpretation and Quantification of Emergency Features on Head Computed Tomography," U.S. Appl. No. 62/269,778, filed Dec. 18, 2015, 44 pages.

Zhao et al., "Synthesizing Filamentary Structured Images with GANs," arXiv:1706.02185v1 [cs.CV], Jun. 7, 2017, 10 pages.

Zhu et al., "Unpaired Image-to-Image Translation using Cycle-Consistent Adversarial Networks," arXiv:1703.10593v4 [cs.CV], Feb. 19, 2018, 20 pages.

\* cited by examiner

APPARATUS, METHODS AND ARTICLES FOR FOUR DIMENSIONAL (4D) FLOW MAGNETIC RESONANCE IMAGING USING COHERENCY IDENTIFICATION FOR MAGNETIC RESONANCE IMAGING FLOW DATA

BACKGROUND

Technical Field

The present disclosure generally relates to magnetic resonance imaging (MRI), and in particular related to four-dimensional (4D) flow MRI.

Description of the Related Art

MRI is most commonly employed in medical imaging, although can be used in other fields. MRI machines include a main magnet which is typically an annular array of coils having a central or longitudinal bore. The main magnet is capable of producing a strong stable magnetic field (e.g., 0.5 Tesla to 3.0 Tesla). The bore is sized to receive at least a portion of an object to be imaged, for instance a human body. When used in medical imaging applications, the MRI machine may include a patient table which allows a prone patient to be easily slid or rolled into and out of the bore.

MRI machines also include gradient magnets. The gradient magnets produce a variable magnetic field that is relatively smaller than that produced by the main magnet (e.g., 180 Gauss to 270 Gauss), allowing selected portions of an object (e.g., patient) to be imaged. MRI machines also include radio frequency (RF) coils which are operated to apply radiofrequency energy to selected portions of the object (e.g., patient) to be imaged. Different RF coils may be used for imaging different structures (e.g., anatomic structures). For example, one set of RF coils may be appropriate for imaging a neck of a patient, while another set of RF coils may be appropriate for imaging a chest or heart of the patient. MRI machines commonly include additional magnets, for example resistive magnets and/or permanent magnets.

The MRI machine typically includes, or is communicatively coupled to a computer system used to control the magnets and/or coils and/or to perform image processing to produce images of the portions of the object being imaged. Conventionally, MRI machines produce magnitude data sets which represent physical structures, for instance anatomical structures. The data sets are often conform to the Digital Imaging and Communications in Medicine (DICOM) standard. DICOM files typically include pixel data and metadata in a prescribed format.

BRIEF SUMMARY

Recently, proposals for producing 4D flow data sets which include anatomical data and velocity in three orthogonal directions, which may be denominated as x velocity, y velocity, and z velocity.

In use, an MRI study may be defined for a single patient session. Each MRI study typically includes several series of perfusion and 4D flow acquisitions, during which multiple sets of MRI data (e.g., 100 images) are acquired for each series. Series may be split into magnitude and phase acquisition portions. The resulting images may be annotated with information.

4D flow pulse sequence MRI has great promise for providing low cost, fast and accurate medical imaging, particularly for cardiac MRI procedures. Some impediments to adoption include high costs. For example, there are high dollar and lost opportunity costs associated with having to have a clinician (e.g., physician) present during the MRI procedure (e.g., acquisition) to assess anatomy during the imaging. There are also high costs associated with the computational powerful computers which are employed at clinical facilities at which the MRI medical imaging is performed and the personnel required to operate and maintain such equipment. Approaches which require breath holding may not be feasible with some patients (e.g., very young or infant). Synchronization of image acquisition with breathing (i.e., pulmonary or respiratory cycles) and/or cardiac cycles also significantly length procedures. Lengthy procedures increase costs as expensive equipment and costly personnel are dedicated to a single patient for the period, reducing throughput. Such also has a tendency to heighten patient anxiety. Not only do these approaches tend to require highly trained technicians and clinicians to be present, but annotation of imaging results tends to be difficult. Further, due to the subjectivity in interpreting the images, for example anatomical structure, there tends to be little repeatability from series to series, let alone from session to session.

Various apparatus, methods and articles are described herein which at least in part address one or more of these issues.

Instead of acquiring only specific planes during MRI acquisition, 4D pulse sequences are employed that acquire a full 3D volume set which includes phase contrast data, hence is denominated as 4D phase contrast MRI. This provides a clinician with the freedom to view any plane they desire, after acquisition without the continued presence of the patient. Error detection and/or correction, segmentation (e.g., delineation of boundaries), quantification, verification and visualization (e.g., fusion of visual representations of flow information with visual representations of anatomy) may be performed on the resulting MRI data set. Much of the image processing and analysis can be performed autonomously (e.g., without intervention of a human).

An MRI image processing and analysis system may be remotely located from one or more MRI acquisition systems, and perform: perform error detection and/or correction on MRI data sets (e.g., phase error correction, phase aliasing, signal unwrapping, and/or on other artifacts); segmentation; visualization of flow (e.g., velocity, arterial versus venous flow, shunts) superimposed on anatomical structure, quantification; verification; and/or generation of patient specific 4-D flow protocols. An asynchronous command and imaging pipeline allows remote image processing and analysis in a timely and secure manner even with complicated or large 4-D flow MRI data sets.

A remote MRI image processing and analysis system may provide cloud based, Web services, or software as services (SAS). The MRI image processing and analysis system employ powerful computational resources, for example large sets or arrays of GPUs. The MRI image processing and analysis system may serve multiple MRI acquisition systems, the MRI acquisition systems operated by one or more diagnostic entities and/or located at one or more diagnostic facilities. This can significantly reduce costs to diagnostic facilities, and the burdens associated with acquiring and maintaining expensive computational equipment.

The approaches described herein may simplify MRI procedures. The approach provides a turn-key system, which captures complete 4D flow images, eliminating the need to have a clinician present during the MRI procedure. The approaches described herein may also significantly shorten the length of MRI procedures. This reduces cost associated with personnel and equipment. This may also increase throughput, allowing capital intensive MRI systems to be amortized over a large number of patients during the equipment's useful life.

The approaches described herein also provide for automated or even autonomous validation of results. Relying on mass conversation principals, at least one approach can identify shunts or other anatomical abnormalities.

Due to enhanced repeatability across a patient or across a population, the approaches described herein may allow identification of new indicators, development of new treatments.

A method of operation for use with magnetic resonance imaging (MRI) based medical imaging systems may be summarized as including receiving a set of MRI data by at least one processor-based device, the set of MRI data comprising respective anatomical structure and blood flow information for each of a plurality of voxels; identifying one or more instances of structure in the set of MRI flow data by at least one processor-based device; and deriving contours in the set of MRI flow data based on the identified one or more instances of structure in the set of MRI flow data by at least one processor-based device. Identifying one or more instances of structure in the set of MRI flow data may include identifying one or more instances of coherency in the set of MRI flow data. Identifying one or more instances of coherency in the set of MRI flow data may include identifying one or more instances of directional coherency in the set of MRI flow data. Identifying one or more instances of coherency in the set of MRI flow data may include identifying one or more instances of directional pathline or structural coherency in the set of MRI flow data. Identifying one or more instances of coherency in the set of MRI flow data may include identifying one or more instances of Discrete Fourier Transform (DFT) component coherency in the set of MRI flow data. Identifying one or more instances of coherency in the set of MRI flow data may include identifying one or more instances of acceleration coherency in the set of MRI flow data.

The may further include identifying one or more instances of clinical markers in the set of MRI flow data, by the at least one processor, based on the identified one or more instances of structure in the set of MRI flow data. Identifying one or more instances of clinical markers in the set of MRI flow data may include identifying one or more instances of anatomical markers and/or temporal markers in the set of MRI flow data. Identifying one or more instances of clinical markers in the set of MRI flow data may include identifying one or more instances of aneurysms, stenosis, or plaque in the set of MRI flow data. Identifying one or more instances of clinical markers in the set of MRI flow data may include identifying one or more pressure gradients in the set of MRI flow data. Identifying one or more instances of clinical markers in the set of MRI flow data may include identifying one or more instances of anatomical landmarks of a heart in the set of MRI flow data. Deriving contours in the set of MRI flow data based on the identified one or more instances of structure in the set of MRI flow data may include deriving contours in the set of MRI flow data that represent various bodily tissues.

The method may further include autonomously segmenting blood bodily tissue from non-blood bodily tissues by at least one processor-based device.

The method may further include autonomously segmenting air from bodily tissues by at least one processor-based device.

A method of operation for use with magnetic resonance imaging (MRI) based medical imaging systems may be summarized as including for a first study of a subject, in a first pass and prior to a first MRI acquisition series: receiving input at a processor-based device, the input specific to the first MRI acquisition; and generating a 4D flow localizer by the processor-based device based at least in part on the received input. Receiving input may include receiving at least one of: a clinical indication, a type or identify of a contrast agent, an amount of contrast agent, a subject's weight, a subject's height, and a subject's heart rate, an amount of time elapsed after bolus provided to subject, an identification of an MRI hardware manufacturer, a type of coil to used, and an identification of at least one characteristic of an MRI machine to be used.

The method may further include for the first study of the subject, in a second pass and prior to a second MRI acquisition series: receiving information about the first MRI acquisition series at a processor-based device; and generating a high fidelity 4D flow localizer by the processor-based device based at least in part on the received information. Receiving information about the first MRI acquisition series at a processor-based device may include receiving output from the first MRI acquisition series. Receiving information about the first MRI acquisition series at a processor-based device may include receiving metrics indicative of a quality of the first MRI acquisition series. Receiving metrics indicative of a quality of the first MRI acquisition series may include at least one rating indicative of a quality of the first MRI acquisition series as assessed by at least one human. Generating a high fidelity 4D flow localizer by the processor-based device based at least in part on the received information may include specifying one or more of: a duration of acquisition, a VENC, a field of view, a repetition time (TR), an echo time (TE), a row resolution, a column resolution, a slice resolution, a temporal resolution, and a flip angle. Generating a high fidelity 4D flow localizer may include determining a value for a velocity encoding (VENC) parameter. Determining a value for a velocity encoding (VENC) parameter may include determining at least an approximation of a velocity of a blood flow in a lumen, and selecting a value for the VENC via a look-up table. Determining a value for a velocity encoding (VENC) parameter may include determining a number of channels of a coil to be used in the acquisition and selecting the value for the VENC based at least in part on the number of channels in the coils.

A processor-based device may have at least one processor and at least one nontransitory processor-readable medium communicatively coupled to the at least one processor, and may be operable to perform any of the previous methods.

A method of operation for use with magnetic resonance imaging (MRI) based medical imaging systems may be summarized as including for a plurality of voxels of an MRI image data set, grouping the voxels into a number of bins by at least one processor-based device; reducing the number of bins via the at least one processor-based device; for a first and a second one of the bins, determining which of the first or the second ones of the bins includes voxels representative of arterial blood flow and which of the first or second one of the bins includes voxels representative of venous blood flow; and assigning a first set of colors to the voxels representative of arterial blood flow and assigning a second set of colors to the voxels representative of venous blood flow, the second set of colors different than the first set of colors. Assigning a first set of colors to the voxels representative of arterial blood flow may include assigning a single blue color to the voxels representative of arterial blood flow and wherein assigning the second set of colors to the voxels representative of venous blood flow may include assigning a single red color to the voxels representative of venous blood flow.

Determining which of the first or the second ones of the bins may include voxels representative of arterial blood flow and which of the first or second one of the bins may include voxels representative of venous blood flow may include determining which of the first or the second ones of the bins may include voxels representative of arterial blood flow and which of the first or second one of the bins may include voxels representative of venous blood flow based on a proximity of at least one of the voxels to a number of anatomical landmarks by the at least one processor-based device. Determining which of the first or the second ones of the bins may include voxels representative of arterial blood flow and which of the first or second one of the bins may include voxels representative of venous blood flow may include determining which of the first or the second ones of the bins may include voxels representative of arterial blood flow and which of the first or second one of the bins may include voxels representative of venous blood flow based on a closet one of the voxels in each bin to a number of anatomical landmarks by the at least one processor-based device.

The method may further include autonomously identifying the anatomical landmarks by the processor-based device.

The method may further include receiving user input that identifies the anatomical landmarks by the processor-based device.

The method may further include for each of at least some of the plurality of voxels, determining whether the respective voxel is representative of blood flow before grouping the voxels into the plurality of bins; and logically marking voxels which are determined to be representative of blood flow. Determining whether the respective voxel may be representative of blood flow may include autonomously determining whether the respective voxel may be representative of blood flow by the at least one processor-based device. Determining whether the respective voxel may be representative of blood flow may include receiving user input indicative of whether the respective voxel may be representative of blood flow by the at least one processor-based device. Reducing the number of bins via the at least one processor-based device may include, where the voxels of one bin spatially contact the voxels of another bin over time, consolidating the voxels into one of the bins.

The method may further include determining if there are more than two bins; and in response to determining if there are more than two bins, determining whether some of the voxels represent a potential shunt by the at least one processor-based device. Determining whether some of the voxels represent a potential shunt by the at least one processor-based device may include identifying areas where adjacent bins are connected by a number of voxels that is less than a defined threshold number of voxels or by an area that is smaller than a defined threshold area.

The method may further include providing a visual emphasis to at least one of voxels that represent the potential shunt or areas at least proximate the potential shunt. Providing a visual emphasis to at least one of voxels that represent the potential shunt or areas at least proximate the potential shunt may include assigning a third set of colors to the voxels that represent the potential shunt or areas at least proximate the potential shunt, the third set of colors different than both the first and the second sets of colors.

The method may further include receiving input by the at least one processor-based device, the input indicative of a human assessment of whether the voxels represent an actual shunt; and updating a color of the voxels that represent the potential shunt based on the received the input indicative of the human assessment of whether the voxels represent an actual shunt. Determining which of the first or the second ones of the bins may include voxels representative of arterial blood flow and which of the first or second one of the bins may include voxels representative of venous blood flow may include for each of at least some of the bins, identifying any voxels in the bin that have a coherence value above a threshold coherence value; for any voxels in the bin that have a coherence value above the threshold coherence value, computing an angle between an average velocity over all of a plurality of time points and a vector that connects a centroid of the respective voxel with a centroid of an anatomical structure; and computing an average angle between all voxels in the bin and the centroid of the anatomical structure.

Determining which of the first or the second ones of the bins may include voxels representative of arterial blood flow and which of the first or second one of the bins may include voxels representative of venous blood flow may further include assigning the bin that has a highest average angle as representing the arterial blood flow; and assigning the bin that has a lowest average angle as representing the venous blood flow. Computing an angle between an average velocity over all of a plurality of time points and a vector that connects a centroid of the respective voxel with a centroid of an anatomical structure may include computing the angle between the average velocity over all of the plurality of time points and the vector that connects the centroid of the respective voxel with the centroid of a heart.

A processor-based device may have at least one processor and at least one nontransitory processor-readable medium communicatively coupled to the at least one processor, and may be operable to perform any of the previous methods.

A method of operation for use with magnetic resonance imaging (MRI) based medical imaging systems may be summarized as including receiving a set of MRI data by at least one processor-based device, the set of MRI data comprising respective anatomical structure and blood flow information for each of a plurality of voxels; and applying a first filter to isolate blood flow based on directional coherence to at least a portion of the received set of MRI data by the at least one processor-based device. Applying a first filter to isolate blood flow based on directional coherence to at least a portion of the received set of MRI data may include for each of a number of voxels, calculating a directional coherence for the respective voxel. Calculating a directional coherence for a respective voxel may include summing a set of weighted directional coherence scores between the respective voxel and a plurality of neighboring voxels which are neighbors of the respective voxel; and dividing a result of the summation by a summation of all weights applied.

The method may further include determining the weighted directional coherence scores between the respective voxel and the plurality of neighboring voxels. Determining the weighted directional coherence scores between the respective voxel and the plurality of neighboring voxels may include determining a dot product of the normalized velocity vectors, applying the trigonometric function ACOS to a result of the dot product to determine an angled difference; scaling the angle difference between 0 and Pi to get a result between 0 and 1; and multiplying the result of the scaling by a respective weight which is indicative of a distance between the respective voxel and a respective one of the neighboring voxels.

The method may further include determining the respective weight. Determining the respective weight may include finding a minimum spacing for all three dimensions, and dividing that minimum spacing by a distance between the voxels. The first filter may be applied in one volume per time point. The first filter may be applied in one volume averaged over all time points per time point.

The method may further include applying a second filter to further remove random noise to the at least a portion of the received set of MRI data by the at least one processor-based device.

A processor-based device may have at least one processor and at least one nontransitory processor-readable medium communicatively coupled to the at least one processor, and may be operable to perform any of the previous methods.

A method of operation for use with magnetic resonance imaging (MRI) based medical imaging systems may be summarized as including receiving a set of MRI data by at least one processor-based device, the set of MRI data comprising respective anatomical structure and blood flow information for each of a plurality of voxels; and identifying an anatomical volume in the set of MRI data; determining a flow of blood into the identified anatomical volume; determining a flow of blood out of the identified anatomical volume; comparing the flow of blood into the identified anatomical volume with the flow of blood out of the identified anatomical volume by the at least one processor-based device.

The method may further include validating a previous operation based on a result of the comparing the flow of blood into the identified anatomical volume with the flow of blood out of the identified anatomical volume.

The method may further include validating a previous segmentation operation based on a result of the comparing the flow of blood into the identified anatomical volume with the flow of blood out of the identified anatomical volume.

The method may further include providing a notification based on a result of the comparing the flow of blood into the identified anatomical volume with the flow of blood out of the identified anatomical volume.

The method may further include providing a notification of a detected shunt based on a result of the comparing the flow of blood into the identified anatomical volume with the flow of blood out of the identified anatomical volume. Identifying an anatomical volume in the set of MRI data may include identifying at least one of a lumen, a portion of a lumen, a vessel, a portion of a vessel, a chamber, or a cavity or a portion of a cavity in an anatomical structure. Identifying an anatomical volume in the set of MRI data may include autonomously identifying the anatomical volume by the at least one processor-based device. Identifying an anatomical volume in the set of MRI data may include autonomously identifying the anatomical volume based on user input received by the at least one processor-based device.

The method may further include identifying a natural entrance to the identified anatomical volume; and Identifying a natural exit of the identified anatomical volume.

The method may further include denominating a first location as an inlet to the identified anatomical volume; and denominating a second location as an outlet from the identified anatomical volume, the second location spaced from the first location. Determining a flow of blood into the identified anatomical volume may include determining a dot product of a normal vector of a first plane that slices the identified anatomical volume at a first location and a velocity vector at each voxel, and determining a flow of blood out of the identified anatomical volume may include determining a dot product of a normal vector of a second plane that slices the identified anatomical volume at a second location and a velocity vector at each voxel, the second location different than the first location.

The method may further include determining a net flow of blood into the identified anatomical volume; and determining a net flow of blood out of the identified anatomical volume. Determining a net flow of blood into the identified anatomical volume may include integrating a result of a dot product of a normal vector of a first plane that slices the identified anatomical volume at a first location and a velocity vector at each voxel over time, and determining a net flow of blood out of the identified anatomical volume may include integrating a result of a dot product of a normal vector of a second plane that slices the identified anatomical volume at a second location and a velocity vector at each voxel over time, the second location different from the first location.

Comparing the flow of blood into the identified anatomical volume with the flow of blood out of the identified anatomical volume may include determining whether the flow values at an inlet and an outlet of the identified anatomical volume match at least within a defined threshold; and may further include in response to determining that the flow values at the inlet and the outlet of the identified anatomical volume do not match at least within the defined threshold, providing an indication of a mismatch. Determining whether the flow values at an inlet and an outlet of the identified anatomical volume match at least within a defined threshold may include autonomously determining whether the flow values at the inlet and the outlet match within the defined threshold by the at least one processor-based device. Comparing the flow of blood into the identified anatomical volume with the flow of blood out of the identified anatomical volume by the at least one processor-based device may include comparing a flow of blood through an ascending thoracic aorta with a combined flow of blood through a superior vena cava and a descending thoracic aorta. Comparing the flow of blood into the identified anatomical volume with the flow of blood out of the identified anatomical volume by the at least one processor-based device may include comparing a combined flow of blood through a superior vena cava and an inferior vena cava with a flow of blood through a set of pulmonary vasculature. Comparing the flow of blood into the identified anatomical volume with the flow of blood out of the identified anatomical volume by the at least one processor-based device may include comparing a flow of blood through the set of pulmonary vasculature with a combined flow of blood through a set of right pulmonary vasculature and a set of left pulmonary vasculature. Comparing the flow of blood into the identified anatomical volume with the flow of blood out of the identified anatomical volume by the at least one processor-based device may include comparing a flow of blood through the set of left pulmonary vasculature to a sum of a flow of blood through all left pulmonary veins. Comparing the flow of blood into the identified anatomical volume with the flow of blood out of the identified anatomical volume by the at least one processor-based device may include comparing a flow of blood through a set of right pulmonary vasculature with a sum of a flow of blood through all right pulmonary veins. Comparing the flow of blood into the identified anatomical volume with the flow of blood out of the identified anatomical volume by the at least one processor-based device may include comparing a flow of blood exiting a cardiac chamber of a heart to a change in a systolic and a diastolic volume for each cardiac chamber of the heart.

A processor-based device may have at least one processor and at least one nontransitory processor-readable medium communicatively coupled to the at least one processor, and may be operable to perform any of the previous methods.

A method of operation for use with magnetic resonance imaging (MRI) based medical imaging systems may be summarized as including receiving a set of MRI data by at least one processor-based device, the set of MRI data comprising respective anatomical structure and blood flow information for each of a plurality of voxels; identifying an anatomical volume in the set of MRI data; identifying a plurality of planes that each intersect a common point and that each cut across the anatomical volume at a respective orientation, the orientations different from one another; and autonomously comparing a flow of blood through each of the planes over a full cardiac cycle by the at least one processor-based device.

Autonomously comparing a flow of blood through each of the planes over a full cardiac cycle includes autonomously determining whether the flow of blood through each of the planes matches at least within some defined threshold over the full cardiac cycle.

The method may further include validating a previous operation based on a result of the comparing the flow of blood through each of the planes over a full cardiac cycle.

The method may further include validating a previous segmentation operation based on a result of the comparing the flow of blood through each of the planes over a full cardiac cycle.

The method may further include providing a notification based on a result of the comparing the flow of blood through each of the planes over a full cardiac cycle.

A processor-based device may have at least one processor and at least one nontransitory processor-readable medium communicatively coupled to the at least one processor, and may be operable to perform any of the previous methods.

A method of operation for use with magnetic resonance imaging (MRI) based medical imaging systems may be summarized as including receiving a set of MRI data by at least one processor-based device, the set of MRI data comprising respective anatomical structure and blood flow velocity information for each of a plurality of voxels; identifying a seed point in a vessel represented in the set of MRI data; identifying a time point with a highest flow magnitude at the seed point; determining a cross sectional plane that is perpendicular to a direction of flow based on both the anatomical structure and blood flow velocity information; and determining a luminal border of the vessel based at least in part on the determined cross sectional plane.

Determining a cross sectional plane that is perpendicular to a direction of flow based on both the anatomical structure and blood flow velocity information may include generating a coarse hemisphere of vectors at the seed point, where any vectors closest to the flow direction have a highest weight; for each of the vectors that make up the coarse hemisphere, casting a plurality of rays perpendicularly to the vector on the coarse hemisphere; and for each of the rays, terminating the respective ray when a magnitude of a change in both an anatomy pixel intensity and a velocity magnitude reaches or exceeds a threshold change.

Determining a cross sectional plane that is perpendicular to a direction of flow based on both the anatomical structure and blood flow velocity information may further include for each of a number of the rays, computing a sum of areas of all of a number of resulting triangles, where the seed point, the termination of the respective ray and the termination of another one of the rays define the resulting triangle; and selecting a vector on the coarse hemisphere that has a smallest computed sum of the areas as a normal vector for a plane that is most perpendicular to the direction of blood flow.

The method may further include resampling a multi-planar reconstruction which combines both the anatomical structure and blood flow velocity information at the initial seed point, along with the strongest flow time point, and with the normal vector.

The method may further include finding a contour that outlines the luminal border of the vessel via an active contour model.

The method may further include applying an energy minimization function using gradient descent to find a smooth contour.

The method may further include determining if a contour diverges by more than a threshold value in area or in curvature; in response to determining that the contour diverges by more than the threshold value in area or in curvature, replacing the contour with a replacement contour that is a linear blend of contours from a plurality of time points adjacent to the time point of the contour being replaced.

A processor-based device may have at least one processor and at least one nontransitory processor-readable medium communicatively coupled to the at least one processor, and may be operable to perform any of the previous methods.

A method of operation for use with magnetic resonance imaging (MRI) based medical imaging systems may be summarized as including receiving a plurality of user events from a plurality of client devices via a first channel of an asynchronous command and image pipeline; capturing at least some of the user events to a persistence layer; determining which of the captured user events to squelch; performing image processing and analysis; and providing a respective response to the user events to the clients via a second channel of the asynchronous command and image pipeline.

Receiving a plurality of user events from a plurality of clients via a first channel of an asynchronous command and image pipeline may include receiving the user events by a server, and may further include providing user events by the server to an MRI image processing and analysis system for image processing and analysis of MRI data sets associated with the user events. Capturing at least some of the user events to a persistence layer and determining which of the captured user events to squelch may include: receiving the user event as a message, and determining whether the image processing and analysis system is busy; and in response to determining that the compute server is not busy, immediately forwarding the message to the compute server. Capturing at least some of the user events to a persistence layer and determining which of the captured user events to squelch may include: receiving the user event as a message, and determining whether the image processing and analysis system is busy; and in response to determining that the compute server is busy, placing the message in a slot.

The method may further include placing a more recent message in the slot that the message placed in the slot.

The method may further include detecting a completion event; and forwarding the respective response to the user event to the respective client. In response to a response that may include image data, sending the response as an HTTPS image request, and HTTPS AJAX request or via a Web socket with binary support. In response to a response that may not include image data, sending the response directly via a Web socket.

The method may further include determining if the is a message in the slot; in response to determining that there is a message in the slot, waiting for a completion event to be detected; in response to detecting the completion event, sending the message from the slot to the compute server; and clearing the slot.

The method may further include rendering multiple images that have linked properties as one larger image; and sending the one large image as a single response.

The method may further include overlaying at least one of lines, markers, or planes in the images before sending the one large image as the single response.

A method of operation for use with magnetic resonance imaging (MRI) based medical imaging systems may be summarized as including providing access to information from a secure clinical facility network through a first firewall by a remote, where all secure patient health information is retained on the secure clinical facility network; securing a MRI image processing and analysis system from the Internet by a second firewall.

A method of operation for use with magnetic resonance imaging (MRI) based medical imaging systems may be summarized as including receiving raw DICOM files by an anonymization service running on a clinical facility network; generating a hash of any plain text patient health information in the raw DICOM file; replacing any plain text patient health information in the raw DICOM file with the respective hash of the plain text patient health information;

The method may further include identifying all patient health information fields in the raw DICOM file, and wherein generating a hash of any plain text patient health information in the raw DICOM file includes generating a salted hash.

The method may further include accessing a key kept within the clinical facility network that turns plain text patient health information into a hash by the anonymization service.

The method may further include allowing access to the anonymization service running on a clinical facility network from outside the clinical facility network only by a VPN of the clinical facility.

A method of operation for use with magnetic resonance imaging (MRI) based medical imaging systems may be summarized as including servicing a plurality of request by a first proxy server, the request coming from with a clinical facility network and from outside the clinical facility network; in response to at least some of the requests, generating plain text information from hashed patient health information by the proxy server; replacing the hashed patient health information with the plain text information by the proxy server; and transmitting the resulting information to a client device.

A method of operation for use with magnetic resonance imaging (MRI) based medical imaging systems may be summarized as including connecting by a client to a server of the MRI image processing and analysis system, the server outside a clinical facility network; checking a flag that indicates whether the client is missing information required to render the patient health information in plain text; in response to an indication that the client is missing information required to render the patient health information in plain text PHI, connecting by the client to an anonymization service; requesting the patient health information in plain text by the client from the anonymization service. Requesting the patient health information in plain text by the client from the anonymization service may include providing a hash or an identifier.

The method may further include caching the received plain text patient health information locally by the client.

The method may further include purging the cached plain text patient health by the client in response to a user logging out.

A method of operation for use with magnetic resonance imaging (MRI) based medical imaging systems may be summarized as including: receiving a set of MRI data by at least one processor-based device, the set of MRI data comprising respective anatomical structure and blood flow information for each of a plurality of voxels; applying a Discrete Fourier Transform (DFT) to each of a plurality of voxels in the set of MRI data over a plurality of available time-points, by the at least one processor-based device; and examining a number of components of the DFT at each of the voxels over the available time-points by the at least one processor-based device.

Applying a DFT to each of a plurality of voxels in the set of MRI data over a plurality of available time-points may include applying a DFT to three velocity components (x, y, z) of the blood flow information. Applying a DFT to each of a plurality of voxels in the set of MRI data over a plurality of available time-points may include applying a DFT to a resulting velocity magnitude of the blood flow information. The method may further include: segmenting a blood pool from static tissue based at least part on the DFT components, by the at least one processor. Segmenting a blood pool from static tissue based at least part on the DFT components may include segmenting the blood pool from the static tissue based at least part on a set of low order, non-DC DFT components, autonomously by the at least one processor. The method may further include: identifying lung tissue in the MRI data. The method may further include: combining a number of DFT components together without regard for relative magnitude or phase to produce a general mask to locate all blood flow within a chest scan, by the at least one processor. The method may further include: combining a number of DFT components together taking into account relative magnitude or phase of the DFT components to produce a refined mask to identify a particular region of a blood pool in the body, by the at least one processor. The method may further include: comparing a phase of the DFT components to a time-point of peak systole, and assigning a probability to each voxel based on an amount of deviation of the phase from an expected value, by the at least one processor. The method may further include: distinguishing between a blood flow in the aorta and a blood flow in the pulmonary arteries based at least in part on the refined mask, by the at least one processor. The method may further include: identifying a probability cutoff value based at least in part on a histogram of the resulting probability values, autonomously by the at least one processor. The method may further include: identifying a probability cutoff value for an arterial specific mask based at least in part on a histogram of the resulting probability values, autonomously by the at least one processor; and determining a probability cutoff values for at least one other mask based at least in part on the arterial specific mask. Determining a probability cutoff values for at least one other mask based at least in part on the arterial specific mask may include performing a flood fill of a general blood mask to remove extraneous non-connected pieces. The method may further include: separating the arterial specific mask into two main portions based at least in part on a number of flow directions and a number or gradients and/or a number of path-lines along with the resulting probability values, by the at least one processor. The method may further include: distinguishing the aorta and the pulmonary artery from one another based at least in part at least one of an average direction of flow or a relative position of the two main portions in space, by the at least one processor. The method may further include: producing a probability mask for a wall of the heart, autonomously by the at least one processor. The method may further include: combining the probability mask for the wall of the heart with a blood flow mask, by the at least one processor. The method may further include: employing the probability mask for the wall of the heart in performing eddy current correction, by the at least one processor. The method may further include: employing the probability mask for the wall of the heart to provide at least one of a location and/or a size of the heart in an image, by the at least one processor.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 4A is a look-up table of exemplary velocity encoding (VENC) values for ranges of flow velocity in bodily vessels or chambers, according to one illustrated embodiment.

FIG. 4B is a look-up table of exemplary values for scan length or duration for a number of channels of a cardiac coil, according to one illustrated embodiment.

DETAILED DESCRIPTION

Figure 1:
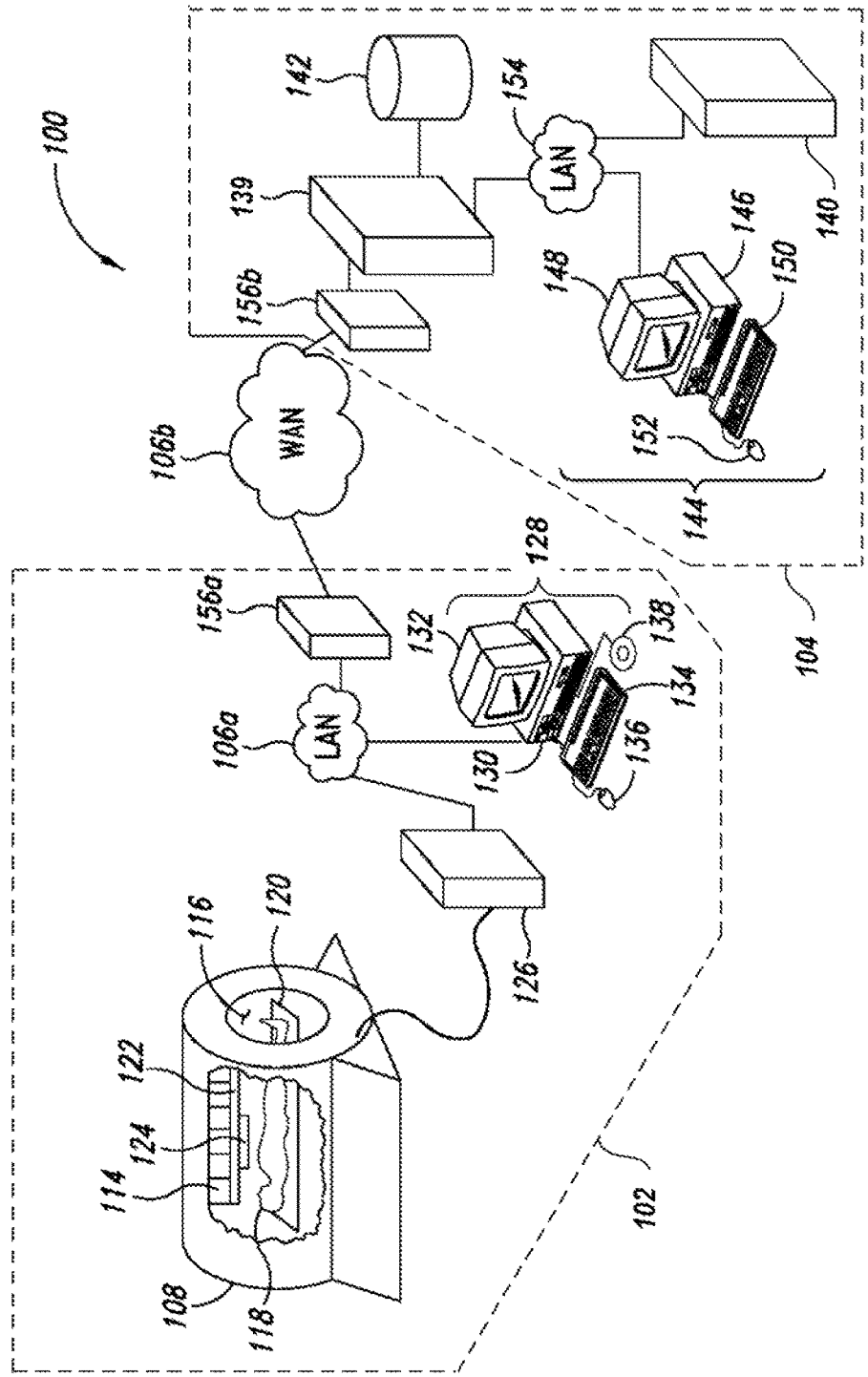
FIG. 1 is a schematic view of a networked environment including at least one MRI acquisition system and at least one image processing system, the MRI acquisition system located in a clinical setting and the image processing system located remotely from the MRI acquisition system and communicatively coupled therewith over one or more networks, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with MRI machines, computer systems, server computers, and/or communications networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are synonymous with "including," and are s inclusive or open-ended (i.e., does not exclude additional, unrecited elements or method acts).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Many of the implementations described herein take advantage of a 4-D flow MRI data set, which essentially captures MRI magnitude and phase information for a three dimensional volume over a period of time. This approach may allow capture or acquisition of MRI data sets without requiring breath holding or synchronization or gating to a patient's cardiac or pulmonary cycles. Instead, MRI data sets are captured or acquired, and imaging processing and analysis employed to derive the desired information, for example by re-binning acquired information based on the cardiac and pulmonary cycles. This essentially pushes what is normally time-intensive acquisition operations to the imaging processing and analysis stage. As way of a simplified analogy, in some respects such may be thought of as capturing a movie of the anatomical structure (e.g., chest, heart) without concern over a patient's pulmonary or cardiac cycles, the processing the captured movie to account for relative movement introduced by the pulmonary and cardiac cycles. The captured information includes both magnitude information, which is indicative of anatomical structure, and phase information which is indicative of velocity. The phase information allows distinction between static and non-static tissue, for example allowing non-static tissue (e.g., blood, air) to be distinguished from static tissue (e.g., fat, bone). The phase information also allows certain non-static tissue (e.g., air) to be distinguished from other non-static tissue (e.g., blood). This may advantageously allow automated or even autonomous segmentation between tissues, and/or distinguishing atrial blood flow from venous blood flow. This may advantageously allow automated or even autonomous generation of flow visualization information, which may be superimposed on anatomical information. This may also advantageously allow automated or even autonomous flow quantification, identifying abnormalities and/or verifying results.

The workflow may general divided into three portions, sequentially: 1) image acquisition, 2) image reconstruction, and 3) image processing or post-processing and analysis. Alternatively, the workflow may be divided into 1) operational, 2) preprocessing, and 3) visualization and quantification.

Image acquisition may include determining, defining, generating or otherwise setting one or more pulse sequences, which are used to run the MRI machine (e.g., control magnets) and acquire raw MRI. Use of a 4D flow pulse sequence allow capture of not only anatomical structure, which is represented by magnitude, but of velocity, which is represented by phase. At least one of the methods or techniques described herein, generation of patient specific 4D pulse sequences, occurs during or as part of image acquisition portion. Image reconstruction may, for example, employ fast Fourier transformations, and result in MRI data sets, often in a form compatible with the DICOM standard. Image reconstruction has traditional been computationally intensive often relying on supercomputers. The requirement for such is a significant burden to many clinical facilities. Many of the methods and techniques described herein occur during or as part of the imaging processor or post-processing and analysis. Such can include error detection and/or error correction, segmentation, visualization including fusion of flow related information and images of anatomical structures, quantification, identification of abnormalities including shunts, verification including identification of spurious data. Alternatively, error detection and/or error correction may occur during the preprocessing portion.

FIG. 1 shows a networked environment 100 according to one illustrated embodiment, in which one or more MRI acquisition system (one shown) 102 are communicatively coupled to at least one image processing and analysis system 104 via one or more networks 106a, 106b (two shown, collectively 106).

The MRI acquisition system 102 is typically located at a clinical facility, for instance a hospital or dedicated medical imaging center. Various techniques and structures, as explained herein, may advantageously allow the image processing and analysis system 104 to be remotely located from the MRI acquisition system 102. The image processing and analysis system 104 may, for example, be located in another building, city, state, province or even country.

The MRI acquisition system 102 may, for example, include an MRI machine 108, a computer system 110 and an MRI operator's system 112. The MRI machine 108 may include a main magnet 114, which is typically an annular array of coils having a central or longitudinal bore 116. The main magnet 108 is capable of producing a strong stable magnetic field (e.g., 0.5 Tesla to 2.0 Tesla). The bore 116 is sized to receive at least a portion of an object to be imaged, for instance a human body 118. When used in medical imaging applications, the MRI machine 108 typically includes a patient table 120 which allows a prone patient 118 to be easily slid or rolled into and out of the bore 116.

The MRI machine also includes a set of gradient magnets 122 (only one called out). The gradient magnets 122 produce a variable magnetic field that is relatively smaller than that produced by the main magnet 114 (e.g., 180 Gauss to 270 Gauss), allowing selected portions of an object (e.g., patient) to be imaged.

MRI machine 108 also include radio frequency (RF) coils 124 (only one called out) which are operated to apply radiofrequency energy to selected portions of the object (e.g., patient 118) to be imaged. Different RF coils 124 may be used for imaging different structures (e.g., anatomic structures). For example, one set of RF coils 124 may be appropriate for imaging a neck of a patient, while another set of RF coils 124 may be appropriate for imaging a chest or heart of the patient. MRI machines 108 commonly include additional magnets, for example resistive magnets and/or permanent magnets.

The MRI machine 108 typically includes, or is communicatively coupled to, a processor-based MRI control system 126 used to control the magnets and/or coils 114, 122, 124. The processor-based control system 126 may include one or more processors, non-transitory computer- or processor-readable memory, drive circuitry and/or interface components to interface with the MRI machine 108. The processor-based control system 126 may, in some implementations, also perform some preprocessing on data resulting from the MRI operation.

An MRI operator's system 128 may include a computer system 130, monitor or display 132, keypad and/or keyboard 134, and/or a cursor control device such as a mouse 136, joystick, trackpad, trackball or the like. The MRI operator's system 128 may include or read computer- or processor executable instructions from one or more non-transitory computer- or processor-readable medium, for instance spinning media 138 such as a magnetic or optical disk. The operator's system 128 may allow a technician to operate the MRI machine 108 to capture MRI data from a patient 118. Various techniques, structures and features described herein may allow MRI machine 108 operation by a technician without requiring the presence of a clinician or physician. Such may advantageously significantly lower costs of MRI procedures. Also as described herein, various techniques, structures and features may allow MRI procedures to be performed much more quickly than using conventional techniques. Such may advantageously allow higher throughput for each MRI installation, amortizing cost of the capital intensive equipment over a much larger number of procedures. For example, high computational power computers may be located remotely from the clinical setting, and may be used to server multiple clinical facilities. The various techniques, structures and features described herein may also additionally or alternatively advantageously reduce the time that each patient is exposed to the MRI procedure, reducing or alleviating the anxiety that often accompanies undergoing an MRI procedure. For instance, eliminating the need for breath holding and/or synchronizing with a patient's pulmonary and/or cardiac cycles via image processing and analysis techniques described herein may significantly reduce the time for acquisition, for example to eight to ten minutes.

The image processing and analysis system 104 may include one or more servers 139 to handle incoming requests and responses, and one or more rendering or image processing and analysis computers 140. The server(s) 139 may, for example take the form of one or more server computers, workstation computers, supercomputers, or personal computers, executing server software or instructions. The one or more rendering or image processing and analysis computers 140 may take the form of one or more computers, workstation computers, supercomputers, or personal computers, executing image processing and/or analysis software or instructions. The one or more rendering or image processing and analysis computers 140 will typically employ one, and preferably multiple, graphical processing units (GPUs) or GPU cores.

The image processing and analysis system 104 may include one or more non-transitory computer-readable medium 142 (e.g., magnetic or optical hard drives, RAID, RAM, Flash) that stores processor-executable instructions and/or data or other information. The image processing and analysis system 104 may include one or more may include one or more image processing and analysis operator's systems 144. The image processing and analysis operator's system 144 may include a computer system 146, monitor or display 148, keypad and/or keyboard 150, and/or a cursor control device such as a mouse 152, joystick, trackpad, trackball or the like. The image processing and analysis operator's system 144 may be communicatively coupled to the rendering or image processing and analysis computer(s) 140 via one or more networks, for instance a LAN 154. While many image processing techniques and analysis may be fully automated, the image processing and analysis operator's system may allow a technician to perform certain image processing and/or analysis operations on MRI data captured from a patient.

While illustrated as a single nontransitory computer- or processor-readable storage medium 142, in many implementations the nontransitory computer- or processor-readable storage medium 142 may constitute a plurality of nontransitory storage media. The plurality of nontransitory storage media may be commonly located at a common location, or distributed at a variety of remote locations. Thus, a database of raw MRI data, preprocessed MRI data and/or processed MRI data may be implemented in one, or across more than one, nontransitory computer- or processor-readable storage media. Such database(s) may be stored separately from one another on separate computer- or processor-readable storage medium 142 or may be stored on the same computer- or processor-readable storage medium 142 as one another. The computer- or processor-readable storage medium 142 may be co-located with the image processing and analysis system 104, for example, in the same room, building or facility. Alternatively, the computer- or processor-readable storage medium 142 may be located remotely from the image processing and analysis system 104, for example, in a different facility, city, state or country. Electronic or digital information, files or records or other collections of information may be stored at specific locations in non-transitory computer- or processor-readable media 142, thus are logically addressable portions of such media, which may or may not be contiguous.

As noted above, the image processing and analysis system 104 may be remotely located from the MRI acquisition system 102. The MRI acquisition system 102 and the image processing and analysis system 104 are capable of communications, for example via one or more communications channels, for example local area networks (LANs) 106a and Wide Area Networks (WANs) 106b. The networks 106 may, for instance include packet switched communications networks, such as the Internet, Worldwide Web portion of the Internet, extranets, and/or intranets. The networks 106 may take the form of various other types of telecommunications networks, such as cellular phone and data networks, and plain old telephone system (POTS) networks. The type of communications infrastructure should not be considered limiting.

As illustrated in FIG. 1, the MRI acquisition system 102 is communicatively coupled to the first LAN 106a. The first LAN 106a may be a network operated by or for the clinical facility, providing local area communications for the clinical facility. The first LAN 106a is communicatively coupled to the WAN (e.g., Internet) 106b. A first firewall 156a may provide security for the first LAN.

Also as illustrated in FIG. 1, the image processing and analysis system 104 is communicatively coupled to the second LAN 154. The second LAN 154 may be a network operated by or for an image processing facility or entity, providing local area communications for the image processing facility or entity. The second LAN 154 is communicatively coupled to the WAN 106b (e.g., Internet). A second firewall 156b may provide security for the second LAN 154.

The image processing facility or entity may be independent from the clinical facility, for example an independent business providing services to one, two or many clinical facilities.

While not illustrated, the communications network may include one or more additional networking devices. The networking devices may take any of a large variety of forms, including servers, routers, network switches, bridges, and/or modems (e.g., DSL modem, cable modem), etc.

While FIG. 1 illustrates a representative networked environment 100, typical networked environments may include many additional MRI acquisition systems, image processing and analysis system 104, computer systems, and/or entities. The concepts taught herein may be employed in a similar fashion with more populated networked environments than that illustrated. For example, a single entity may provide image processing and analysis services to multiple diagnostic entities. One or more of the diagnostic entities may operate two or more MRI acquisition systems 102. For example, a large hospital or dedicated medical imaging center may operate two, three or even more MRI acquisition systems at a single facility. Typically, the entity that provides the image processing and analysis services will operate multiple entity may provide image processing and analysis systems 104 which may include two, three or even hundreds of rendering or image processing and analysis computers 140.

Figure 2:
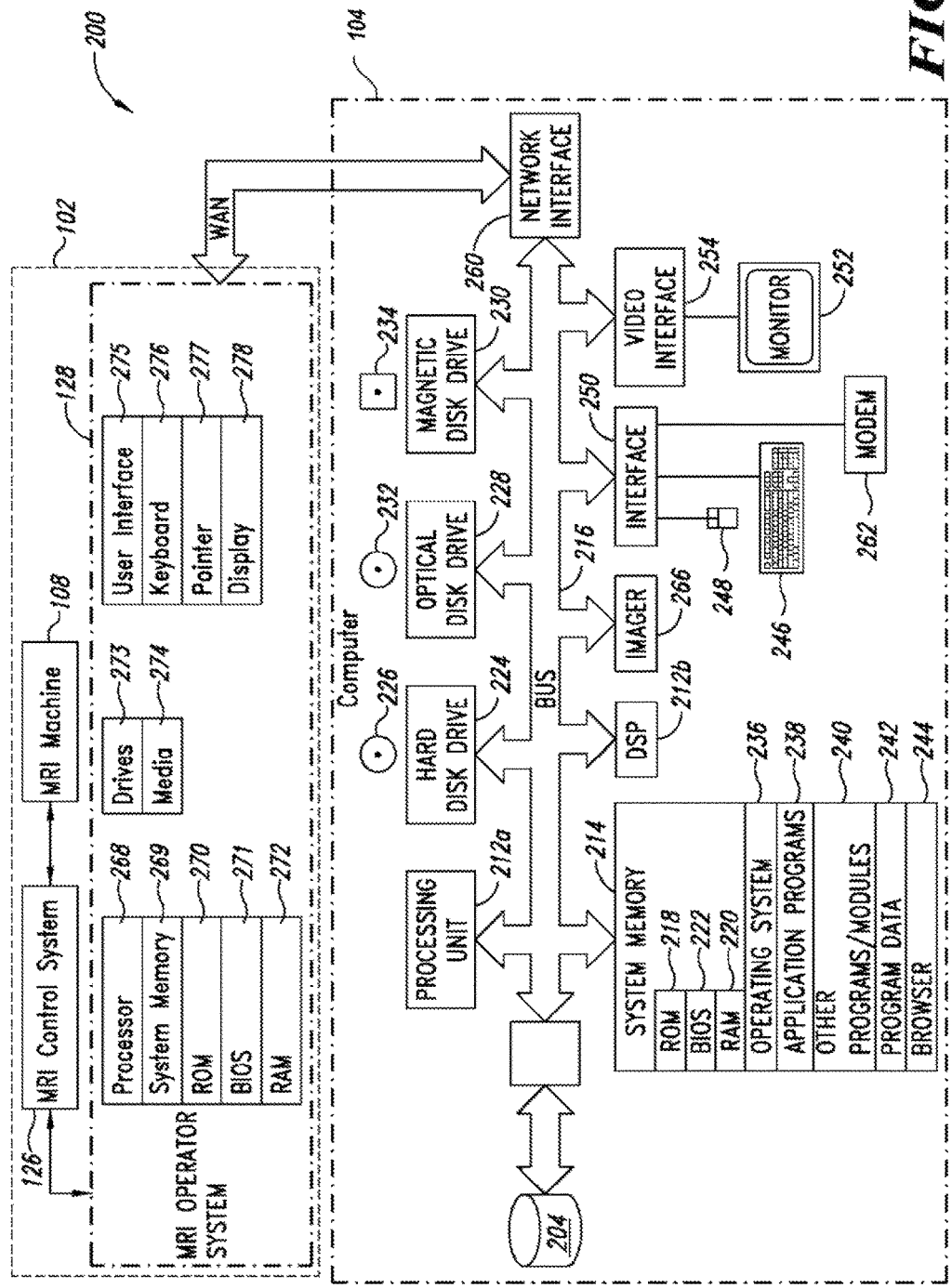
FIG. 2 is a functional block diagram of an MRI acquisition system and an MRI image processing and analysis system that provides MRI image processing and analysis services, according to one illustrated embodiment.

FIG. 2 shows a networked environment 200 comprising one or more image processing and analysis systems 104 (only one illustrated) and one or more associated nontransitory computer- or processor-readable storage medium 204 (only one illustrated). The associated nontransitory computer- or processor-readable storage medium 204 is communicatively coupled to the image processing and analysis system(s) 104 via one or more communications channels, for example, one or more parallel cables, serial cables, or wireless channels capable of high speed communications, for instance, via FireWire®, Universal Serial Bus® (USB) 2 or 3, and/or Thunderbolt®, Gigabyte Ethernet®.

The networked environment 200 also comprises one or more end MRI acquisition systems 102 (only one illustrated). The MRI acquisition system(s) 102 are communicatively coupled to the image processing and analysis system(s) 104 by one or more communications channels, for example, one or more wide area networks (WANs) 210, for instance the Internet or Worldwide Web portion thereof.

In operation, the MRI acquisition systems 102 typically function as a client to the image processing and analysis system 104. In operation, the image processing and analysis systems 104 typically functions as a server to receive requests or information (e.g., MRI data sets) from the MRI acquisition systems 102. Described herein is an overall process which employs an asynchronous command and imaging pipeline that allows the image processing and analysis to be performed remotely (e.g., over a WAN) from the MRI acquisition system 102. This approach provides for a number of distinctive advantages, for instance allowing the MRI acquisition system(s) 102 to be operated by a technician without requiring the presence of a clinician (e.g., physician). Various techniques or approaches are also described to enhance security, while allowing access to medical imaging data as well as private patient specific health information.

While illustrated as located remotely from the MRI acquisition system(s) 102, in some implementations the image processing and analysis systems 104 may be co-located with the MRI acquisition system 102. In other implementations, one or more of the operations or functions described herein may be performed by the MRI acquisition system 102 or via a processor-based device co-located with the MRI acquisition system 102.

The image processing and analysis systems 104 receive MRI data sets, perform image processing on the MRI data sets, and provide the processed MRI data sets, for example to a clinician for review. The image processing and analysis systems 104 may, for example, perform error detection and/or correction on MRI data sets, for example phase error correction, phase aliasing detection, signal unwrapping, and/or detection and/or correction of various artifacts. Phase error is related to phase, as is phase aliasing. Signal unwrapping is related to magnitude. Various other artifacts may be related to phase and/or magnitude.

The image processing and analysis systems 104 may, for example, perform segmentation, distinguishing between various tissue type. The image processing and analysis systems 104 may, for example, perform quantification, for instance comparing blood flow into and out of a closed anatomical structure or through two or more anatomical structures. The image processing and analysis systems 104 may advantageously use quantification to verify results, for example confirming identification of a certain tissue and/or providing an indication of an amount of certainty in the results. Additionally, the image processing and analysis systems 104 may advantageously use quantification to identify the existence of a shunt.

In some implementations, the image processing and analysis systems 104 may generate images which reflect blood flow, for example including distinguishing between arterial and venous blood flow. For instance, the image processing and analysis systems 104 may employ a first color map (e.g., blue) to indicate arterial blood flow and a second color map (e.g., red) to indicate venous blood flow. The image processing and analysis systems 104 may indicate aberrations (e.g., shunt) using some other, distinctive color or visual emphasis. Numerous different techniques are described for distinguishing between different tissues as wells as between arterial and venous blood flow. Flow visualization may be superimposed, for instance as one or more layers, on or over visual representations of anatomical structure or magnitude data.

In some implementations, the image processing and analysis systems 104 may generate a patient specific 4D-flow protocol for use in operating an MRI acquisition system 102 with a specific patient. Such may include setting an appropriate velocity encoding (VENC) for operation of the MRI machine.

The image processing and analysis systems 104 may perform one or more of these operations or functions autonomously, without human input. Alternatively, the image processing and analysis systems 104 may perform one or more of these operations or functions based on human input, for example human input which identifies a point, location or plane, or which otherwise identifies a characteristic of anatomical tissue. Some planes and/or views may be predefined, allowing the operator, user or clinician to simply select a plane (e.g., a valve plane) or a denominated view (e.g., 2 chamber view, 3 chamber view, 4 chamber view) to quickly and easily obtain the desired view.

The networked environment 200 may employ other computer systems and network equipment, for example, additional servers, proxy servers, firewalls, routers and/or bridges. The image processing and analysis systems 104 will at times be referred to in the singular herein, but this is not intended to limit the embodiments to a single device since in typical embodiments there may be more than one image processing and analysis systems 104 involved. Unless described otherwise, the construction and operation of the various blocks shown in FIG. 2 are of conventional design. As a result, such blocks need not be described in further detail herein, as they will be understood by those skilled in the relevant art.

The image processing and analysis systems 104 may include one or more processing units 212a, 212b (collectively 212), a system memory 214 and a system bus 216 that couples various system components, including the system memory 214 to the processing units 212. The processing units 212 may be any logic processing unit, such as one or more central processing units (CPUs) 212a, digital signal processors (DSPs) 212b, application-specific integrated circuits (ASICs), field programmable gate arrays (FPGAs), etc. The system bus 216 can employ any known bus structures or architectures, including a memory bus with memory controller, a peripheral bus, and/or a local bus. The system memory 214 includes read-only memory ("ROM") 218 and random access memory ("RAM") 220. A basic input/output system ("BIOS") 222, which can form part of the ROM 218, contains basic routines that help transfer information between elements within the image processing and analysis system(s) 104, such as during start-up.

The image processing and analysis system(s) 104 may include a hard disk drive 224 for reading from and writing to a hard disk 226, an optical disk drive 228 for reading from and writing to removable optical disks 232, and/or a magnetic disk drive 230 for reading from and writing to magnetic disks 234. The optical disk 232 can be a CD-ROM, while the magnetic disk 234 can be a magnetic floppy disk or diskette. The hard disk drive 224, optical disk drive 228 and magnetic disk drive 230 may communicate with the processing unit 212 via the system bus 216. The hard disk drive 224, optical disk drive 228 and magnetic disk drive 230 may include interfaces or controllers (not shown) coupled between such drives and the system bus 216, as is known by those skilled in the relevant art. The drives 224, 228 and 230, and their associated computer-readable media 226, 232, 234, provide nonvolatile storage of computer-readable instructions, data structures, program modules and other data for the image processing and analysis system(s) 104. Although the depicted image processing and analysis systems 104 is illustrated employing a hard disk 224, optical disk 228 and magnetic disk 230, those skilled in the relevant art will appreciate that other types of computer-readable media that can store data accessible by a computer may be employed, such as WORM drives, RAID drives, magnetic cassettes, flash memory cards, digital video disks ("DVD"), Bernoulli cartridges, RAMs, ROMs, smart cards, etc.

Program modules can be stored in the system memory 214, such as an operating system 236, one or more application programs 238, other programs or modules 240 and program data 242. Application programs 238 may include instructions that cause the processor(s) 212 to perform image processing and analysis on MRI image data sets. For example, the application programs 238 may include instructions that cause the processor(s) 212 to perform phase error correction on phase or velocity related data. For example, the application programs 238 may include instructions that cause the processor(s) 212 to correct for phase aliasing. Also for example, the application programs 238 may include instructions that cause the processor(s) 212 to perform signal unwrapping. Additionally or alternatively, the application programs 238 may include instructions that cause the processor(s) 212 to identify and/or correct for artifacts.

The application programs 238 may include instructions that cause the processor(s) 212 to, for example, perform segmentation, distinguishing between various tissue type. The application programs 238 may include instructions that cause the processor(s) 212 to perform quantification, for instance comparing blood flow into and out of a closed anatomical structure or through two or more anatomical structures. The application programs 238 may include instructions that cause the processor(s) 212 to use quantification to verify results, for example confirming identification of a certain tissue and/or providing an indication of an amount of certainty in the results. The application programs 238 may include instructions that cause the processor(s) 212 to use quantification to identify the existence of a shunt.

The application programs 238 may include instructions that cause the processor(s) 212 to generate images which reflect blood flow, for example distinguishing between arterial and venous blood flow. For instance, a first color map (e.g., blue) may be used to indicate arterial blood flow and a second color map (e.g., red) to indicate venous blood flow. Aberrations (e.g., shunt) may be indicated using some other, distinctive color or visual emphasis. Color transfer functions may be applied to generate the color maps. The application programs 238 may include instructions that cause the processor(s) 212 to superimpose visualization of flow (e.g., MRI phase data indicative of blood flow velocity and/or volume) on visualization or rendered images of anatomy (e.g., MRI magnitude data). The instructions may cause the flow visualization to be rendered as one or more layers on the images of the anatomy to provide a fusion of anatomy (i.e., magnitude) and flow (i.e., phase) information, for example as a color heat map and/or as vectors (e.g., arrow icons) with direction and magnitude (e.g., represented by length, line weight). The instructions may additionally or alternatively cause the generation of spatial mappings or visualization of signal dispersion, turbulence and/or pressure, which may be overlaid or superimposed on a spatial mapping or visualization of anatomical structure. Fusing visualization of phase or velocity related information with visualization of anatomical information or visual representations of anatomical structures may facilitate the identification of anatomical landmarks. The instructions may make use of sets or arrays of graphics processing units or GPUs to quickly render the visualizations.

Transfer functions may also be applied to determine which visual effects (e.g., color) to apply to which tissue. For example, arterial blood flow may be colored in shades of blue and venous blood flow in shades of red, while fat tissue colored as yellow. Anatomical structure, represented as magnitude in the MRI image data set, may, for example, be visualized using grey scale. Depth of view may be operator or user adjustable, for example via a slider control on a graphical user interface. Thus, visualization may be in the form a fusion view that advantageously fuses a visual representation of velocity information with a visual representation of anatomical information or representation.

The application programs 238 may include instructions that cause the processor(s) 212 to generate a patient specific 4D-flow protocol for use in operating an MRI acquisition system 102 with a specific patient. Such may be based on patient specific input, for example provided by a technician, and may be based on the particular MRI machine being used to capture the MRI data set.

The application programs 238 may include instructions that cause the processor(s) 212 to receive image data sets from the MRI acquisition system, process and/or analyze the image data sets, and provide processed and/or analyzed images and other information to users remotely located from the image processing, in a time sensitive and secure manner. Such is described in detail herein with reference to the various Figures.

The system memory 214 may also include communications programs, for example, a server 244 that causes the image processing and analysis system(s) 104 to serve electronic information or files via the Internet, intranets, extranets, telecommunications networks, or other networks as described below. The server 244 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document. A number of suitable servers may be commercially available such as those from Mozilla, Google, Microsoft and Apple Computer.

While shown in FIG. 2 as being stored in the system memory 214, the operating system 236, application programs 238, other programs/modules 240, program data 242 and server 244 can be stored on the hard disk 226 of the hard disk drive 224, the optical disk 232 of the optical disk drive 228 and/or the magnetic disk 234 of the magnetic disk drive 230.

An operator can enter commands and information into the image processing and analysis system(s) 104 through input devices such as a touch screen or keyboard 246 and/or a pointing device such as a mouse 248, and/or via a graphical user interface. Other input devices can include a microphone, joystick, game pad, tablet, scanner, etc. These and other input devices are connected to one or more of the processing units 212 through an interface 250 such as a serial port interface that couples to the system bus 216, although other interfaces such as a parallel port, a game port or a wireless interface or a universal serial bus ("USB") can be used. A monitor 252 or other display device is coupled to the system bus 216 via a video interface 254, such as a video adapter. The image processing and analysis system(s) 104 can include other output devices, such as speakers, printers, etc.

The image processing and analysis systems 104 can operate in a networked environment 200 using logical connections to one or more remote computers and/or devices. For example, the image processing and analysis 104 can operate in a networked environment 200 using logical connections to one or more MRI acquisition systems 102. Communications may be via a wired and/or wireless network architecture, for instance, wired and wireless enterprise-wide computer networks, intranets, extranets, and/or the Internet. Other embodiments may include other types of communications networks including telecommunications networks, cellular networks, paging networks, and other mobile networks. There may be any variety of computers, switching devices, routers, bridges, firewalls and other devices in the communications paths between the image processing and analysis systems 104, the MRI acquisition systems 102.

The MRI acquisition systems 102 will typically take the form of an MRI machine 108 and one or more associated processor-based devices, for instance an MRI control system 126 and/or MRI operator's system 128. The MRI acquisition systems 102 capture MRI information or data sets from patients. Thus, in some instances the MRI acquisition systems 102 may be denominated as front end MRI acquisition systems or MRI capture systems, to distinguish such from the MRI image processing and analysis system(s) 104, which in some instances may be denominated as MRI backend systems. The MRI acquisition systems 102 will at times each be referred to in the singular herein, but this is not intended to limit the embodiments to a single MRI acquisition system 102. In typical embodiments, there may be more than one MRI acquisition system 102 and there will likely be a large number of MRI acquisition systems 102 in the networked environment 200.

The MRI acquisition systems 102 may be communicatively coupled to one or more server computers (not shown). For instance, MRI acquisition systems 102 may be communicatively coupled via one or more diagnostic facility server computers (not shown), routers (not shown), bridges (not shown), LANs 106a (FIG. 1), etc., which may include or implement a firewall 156a (FIG. 1). The server computers (not shown) may execute a set of server instructions to function as a server for a number of MRI acquisition systems 102 (i.e., clients) communicatively coupled via a LAN 106a at a clinical facility or site, and thus act as intermediaries between the MRI acquisition systems 102 and the MRI image processing and analysis system(s) 104. The MRI acquisition systems 102 may execute a set of client instructions to function as a client of the server computer(s), which are communicatively coupled via a WAN.

The MRI control system 126 typically includes one or more processor (e.g., microprocessors, central processing units, digital signal processors, graphical processing units) and non-transitory processor-readable memory (e.g., ROM, RAM, Flash, magnetic and/or optical disks). The MRI operator's system 128 may take the form of a computer, for instance personal computers (e.g., desktop or laptop computers), net book computers, tablet computers, smart phones, personal digital assistants, workstation computers and/or mainframe computers, and the like, executing appropriate instructions.

The MRI operator's system 128 may include one or more processing units 268, system memories 269 and a system bus (not shown) that couples various system components including the system memory 269 to the processing unit 268.

The processing unit 268 may be any logic processing unit, such as one or more central processing units (CPUs), digital signal processors (DSPs), application-specific integrated circuits (ASICs), field programmable gate arrays (FPGAs), graphical processing units (GPUs), etc. Non-limiting examples of commercially available computer systems include, but are not limited to, an 80x86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, a 68xxx series microprocessor from Motorola Corporation, an ATOM processor, or an A4 or A5 processor. Unless described otherwise, the construction and operation of the various blocks of the MRI acquisition systems 102 shown in FIG. 2 are of conventional design. As a result, such blocks need not be described in further detail herein, as they will be understood by those skilled in the relevant art.

The system bus can employ any known bus structures or architectures, including a memory bus with memory controller, a peripheral bus, and a local bus. The system memory 269 includes read-only memory ("ROM") 270 and random access memory ("RAM") 272. A basic input/output system ("BIOS") 271, which can form part of the ROM 270, contains basic routines that help transfer information between elements within the MRI acquisition systems 102, such as during start-up.

The MRI operator's system 128 may also include one or more media drives 273, e.g., a hard disk drive, magnetic disk drive, WORM drive, and/or optical disk drive, for reading from and writing to computer-readable storage media 274, e.g., hard disk, optical disks, and/or magnetic disks. The nontransitory computer-readable storage media 274 may, for example, take the form of removable media. For example, hard disks may take the form of a Winchester drive, and optical disks can take the form of CD-ROMs, while magnetic disks can take the form of magnetic floppy disks or diskettes. The media drive(s) 273 communicate with the processing unit 268 via one or more system buses. The media drives 273 may include interfaces or controllers (not shown) coupled between such drives and the system bus, as is known by those skilled in the relevant art. The media drives 273, and their associated nontransitory computer-readable storage media 274, provide nonvolatile storage of computer readable instructions, data structures, program modules and other data for MRI acquisition system(s) 102. Although described as employing computer-readable storage media 274 such as hard disks, optical disks and magnetic disks, those skilled in the relevant art will appreciate that MRI operator's system(s) 128 may employ other types of nontransitory computer-readable storage media that can store data accessible by a computer, such as magnetic cassettes, flash memory cards, digital video disks ("DVD"), Bernoulli cartridges, RAMs, ROMs, smart cards, etc. Data or information, for example, electronic or digital files or data or metadata related to such can be stored in the nontransitory computer-readable storage media 274.

Program modules, such as an operating system, one or more application programs, other programs or modules and program data, can be stored in the system memory 269. Program modules may include instructions for accessing a Website, extranet site or other site or services (e.g., Web services) and associated Webpages, other pages, screens or services hosted or provided by the MRI processing and analysis system(s) 104.

In particular, the system memory 269 may include communications programs that permit the MRI acquisition system(s) 102 to exchange electronic or digital information or files or data or metadata with the MRI image processing and/or analysis services provided by the MRI processing and analysis system(s) 104. The communications programs may, for example, be a Web client or browser that permits the MRI acquisition system(s) 102 to access and exchange information, files, data and/or metadata with sources such as Web sites of the Internet, corporate intranets, extranets, or other networks. Such may require that an end user client have sufficient right, permission, privilege or authority for accessing a given Website, for example, one hosted by the MRI processing and analysis system(s) 104. As discussed herein, patient identifying data may reside on systems operated by or for the clinical facility, and may not be accessible by or through the systems operated by or for the image processing facility or the image processing facility personnel. The browser may, for example, be markup language based, such as Hypertext Markup Language (HTML), Extensible Markup Language (XML) or Wireless Markup Language (WML), and may operate with markup languages that use syntactically delimited characters added to the data of a document to represent the structure of the document.

While described as being stored in the system memory 269, the operating system, application programs, other programs/modules, program data and/or browser can be stored on the computer-readable storage media 274 of the media drive(s) 273. An operator can enter commands and information into the MRI operator's system(s) 128 via a user interface 275 through input devices such as a touch screen or keyboard 276 and/or a pointing device 277 such as a mouse. Other input devices can include a microphone, joystick, game pad, tablet, scanner, etc. These and other input devices are connected to the processing unit 269 through an interface such as a serial port interface that couples to the system bus, although other interfaces such as a parallel port, a game port or a wireless interface or a universal serial bus ("USB") can be used. A display or monitor 278 may be coupled to the system bus via a video interface, such as a video adapter. The MRI operator system(s) 128 can include other output devices, such as speakers, printers, etc.

The MRI image processing and analysis system may build a static interface, which allows various tissue types to be subtracted or added to an MRI 4D flow data set. For example, static tissues such as fat or bone may be distinguished from non-static tissues such as air or flowing blood. The MRI image processing and analysis system may further autonomously distinguish between various non-static tissues, for instance distinguishing between air (e.g., lungs) and flowing blood. Further, the MRI image processing and analysis system may distinguish between arterial and venous blood flows.

For instance, the MRI image processing and analysis system may employ fast Fourier transformation to identify blood tissue, which is expected to have a pulsatile pattern or waveform. Air or lung will tend to have a random appear pattern over a defined volume, as velocity of neighboring voxels are compared. For instance, voxels with strong or fast velocities are typically indicative or air. The MRI data sets may be rather large, for example 256×256×256×20 time points. The MRI image processing and analysis system may rely on gradients (e.g., gradient descent method) to detect different tissue types, and may advantageously employ a numerical approach rather than an analytic solution approach to quickly handle the relatively large MRI data sets. By controlling the number of significant digits (e.g., 2) of the numerical approach, the MRI image processing and analysis system may achieve very fast (e.g., 1 second as opposed to 30 minutes) results, while still obtaining results that are sufficiently accurate for the particular application.

In some implementations, different tissue types may be subtracted from the patient MRI data set, one at a time. For example, subtracting air or lung, subtracting blood, separating atrial from venous flow, subtracting bone, leaving fat. Notably, fat is static, so each voxel representing fat should have zero velocity associated therewith. The MRI image processing and analysis system may advantageously employ such a ground truth to correct MRI data set for all tissue types.

If a non-zero velocity is found for fat type tissue, this can be used to adjust the entire set of data (e.g., for all tissue). For example, the MRI image processing and analysis system may generate or create a polynomial model based on an identified area or volume (e.g., fat or soft tissue). Such may be a simple polynomial (e.g., $ax^2+bx+c$) or a much more complex polynomial (e.g., non-rational uniform b-spline). The MRI image processing and analysis system may find the coefficients to the polynomial fits the image, for example using linear regression techniques or linear algebra techniques. This results in a model which the MRI image processing and analysis system may apply to (e.g., subtract from) the whole field, not just the fat or soft tissue.

In one implementations, a replica body is imaged to create a reference set of data or "phantom" model which can be subtracted from actually patient data. The replica body may be formed of materials that mimic the MRI response of an actually body, although will not have blood flow. A phase gradient in reference set of data or "phantom" model may represent noise (e.g., random noise), and can be used to correct a phase shift. This approach advantageously avoids the need to generate a polynomial fit to the 3D data. The generated reference set or phantom model may be valid over a number of months of MRI machine operation, although a new set of reference data or phantom model should be generated if the MRI machine is serviced or moved.

The MRI image processing and analysis system may define various filters or mask for removing different tissue types or for removing either venous or atrial blood flow. Filters or masks may remove anomalous blood flow, such as blood flow outside some reasonable range (e.g., too high or fast, too slow or low) or where blood appears to be flowing in an anatomical structure (e.g., bone) where there should be no blood flow. A filter or mask may also be defined to display only voxels having magnitudes with an absolute value greater than some threshold value. A filter or mask may also be defined to display only voxels with an absolute value of the cross product of magnitude and a velocity vector which absolute value is greater than some defined threshold. Further a filter or mask may be defined that shows only voxels having vectors in a same direction as the vectors of neighboring voxels, to for instance identify or view high velocity jets. Notably, velocity vectors of neighboring voxels are in different directions may be an indication of noise.

Figure 3A:
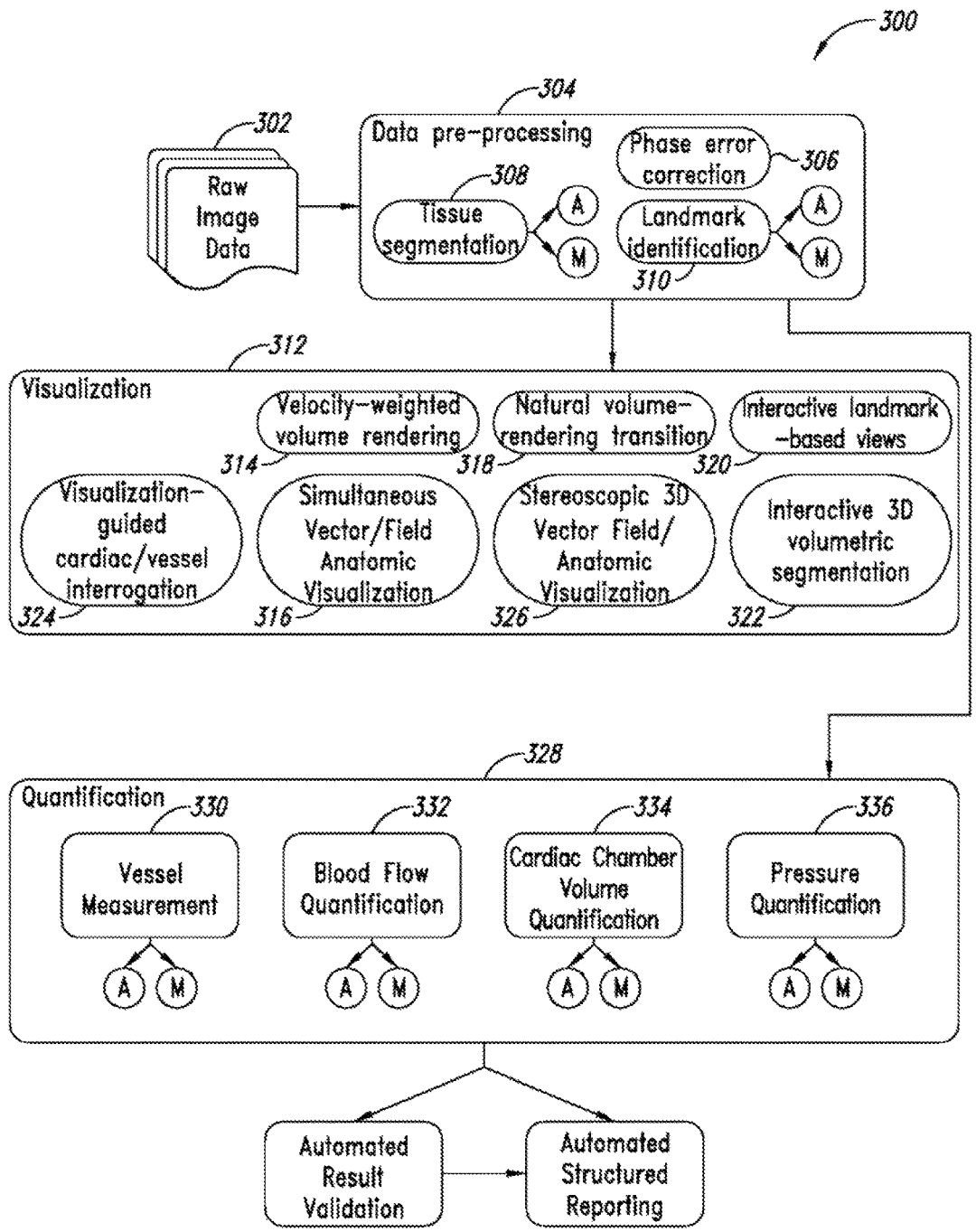
FIG. 3A is a schematic view of a data flow in an MRI image processing and analysis or rendering system, according to one illustrated embodiment.

FIG. 3A shows a representative data flow 300 in an MRI image processing and analysis or rendering system, according to one illustrated embodiment.

The MRI image processing and analysis system 104 (FIG. 1) receives "raw" MRI image data 302, for example in the form of DICOM standard compliant electronic files. In some implementations, the "raw" MRI image data 302 may have had some minimal level of image preprocessing performed, for example by a processor-based system associated with the acquisition portion (MRI acquisition system 102, FIG. 1).

At 304, the MRI image processing and analysis system performs data pre-processing on the "raw" data.

The pre-processing may, for example, include, phase error correction 306 which the MRI image processing and analysis system may be perform autonomously. Various suitable approaches to phase error correction 306 are discussed elsewhere herein.

As part of pre-processing 304, the MRI image processing and analysis system may, for example, perform tissue segmentation at 308. The MRI image processing and analysis system may be perform the tissue segmentation 306 autonomously, as indicated by a circle enclosing the letter A. Alternatively or additionally, the MRI image processing and analysis system may be perform the tissue segmentation 308 manually as indicated by a circle enclosing the letter M, for instance via interaction (e.g., receipt of input from a human) with the MRI image processing and analysis system. Various suitable approaches to tissue segmentation 306 are discussed elsewhere herein.

As part of pre-processing 304, the MRI image processing and analysis system may, for example, perform landmark identification at 310. The MRI image processing and analysis system may be perform the landmark identification 310 autonomously, as indicated by a circle enclosing the letter A. Alternatively or additionally, the MRI image processing and analysis system may be perform the landmark identification 310 manually as indicated by a circle enclosing the letter M, for instance via interaction (e.g., receipt of input from a human) with the MRI image processing and analysis system. Various suitable approaches to landmark identification 310 are discussed elsewhere herein.

At 312, the MRI image processing and analysis system performs visualization on the pre-processing data.

As part of visualization 312, the MRI image processing and analysis system may, for example, perform velocity weighted volume rendering at 314. Various suitable approaches to velocity weighted volume rendering 314 are discussed elsewhere herein.

As part of visualization 312, the MRI image processing and analysis system may, for example, perform simultaneous vector field and anatomical structure visualization or rendering at 316. Various suitable approaches to simultaneous vector field and anatomical structure visualization or rendering 316 are discussed elsewhere herein.

As part of visualization 312, the MRI image processing and analysis system may, for example, perform natural volume rendering transition at 318. Various suitable approaches to natural volume rendering transition 318 are discussed elsewhere herein.

As part of visualization 312, the MRI image processing and analysis system may, for example, provide for or produce interactive landmarked based view at 320. Various suitable approaches to providing interactive landmarked based view 320 are discussed elsewhere herein.

As part of visualization 312, the MRI image processing and analysis system may, for example, perform or provide interactive 3D volumetric segmentation at 322. Various suitable approaches to providing interactive 3D volumetric segmentation 322 are discussed elsewhere herein.

As part of visualization 312, the MRI image processing and analysis system may, for example, perform visualization guided cardiac and/or vessel interrogation at 324. Various suitable approaches to performing or providing visualization guided cardiac and/or vessel interrogation 324 are discussed elsewhere herein.

As part of visualization 312, the MRI image processing and analysis system may, for example, perform or provide stereoscopic 3D vector field and anatomic visualization at 326. Various suitable approaches to providing for stereoscopic 3D vector field and anatomic visualization 326 are discussed elsewhere herein.

At 328, the MRI image processing and analysis system performs visualization on the pre-processing data.

As part of performing quantification, 328, the MRI image processing and analysis system may, for example, perform vessel measurement at 330. The MRI image processing and analysis system may be perform the vessel measurement 330 autonomously, as indicated by a circle enclosing the letter A. Alternatively or additionally, the MRI image processing and analysis system may be perform the vessel measurement 330 manually as indicated by a circle enclosing the letter M, for instance via interaction (e.g., receipt of input from a human) with the MRI image processing and analysis system. Various suitable approaches to vessel measurement 330 are discussed elsewhere herein.

As part of performing quantification, 328, the MRI image processing and analysis system may, for example, perform blood flow quantification at 332. The MRI image processing and analysis system may be perform the blood flow quantification 332 autonomously, as indicated by a circle enclosing the letter A. Alternatively or additionally, the MRI image processing and analysis system may be perform the blood flow quantification 332 manually as indicated by a circle enclosing the letter M, for instance via interaction (e.g., receipt of input from a human) with the MRI image processing and analysis system. Various suitable approaches to blood flow quantification 332 are discussed elsewhere herein.

As part of performing quantification, 328, the MRI image processing and analysis system may, for example, perform cardiac chamber volume quantification at 334. The MRI image processing and analysis system may be perform the cardiac chamber volume quantification 334 autonomously, as indicated by a circle enclosing the letter A. Alternatively or additionally, the MRI image processing and analysis system may be perform the cardiac chamber volume quantification 334 manually as indicated by a circle enclosing the letter M, for instance via interaction (e.g., receipt of input from a human) with the MRI image processing and analysis system. Various suitable approaches to cardiac chamber volume quantification 334 are discussed elsewhere herein.

As part of performing quantification, 328, the MRI image processing and analysis system may, for example, perform pressure quantification at 336. The MRI image processing and analysis system may be perform the pressure quantification 336 autonomously, as indicated by a circle enclosing the letter A. Alternatively or additionally, the MRI image processing and analysis system may be perform the pressure quantification 336 manually as indicated by a circle enclosing the letter M, for instance via interaction (e.g., receipt of input from a human) with the MRI image processing and analysis system. Various suitable approaches to pressure quantification 336 are discussed elsewhere herein.

At 338, the MRI image processing and analysis system performs automated result validation. Various suitable approaches to performing automated result validation 338 are discussed elsewhere herein.

At 340, the MRI image processing and analysis system performs automated structure reporting. Various suitable approaches to performing automated structure reporting 340 are discussed elsewhere herein.

Figure 3B:
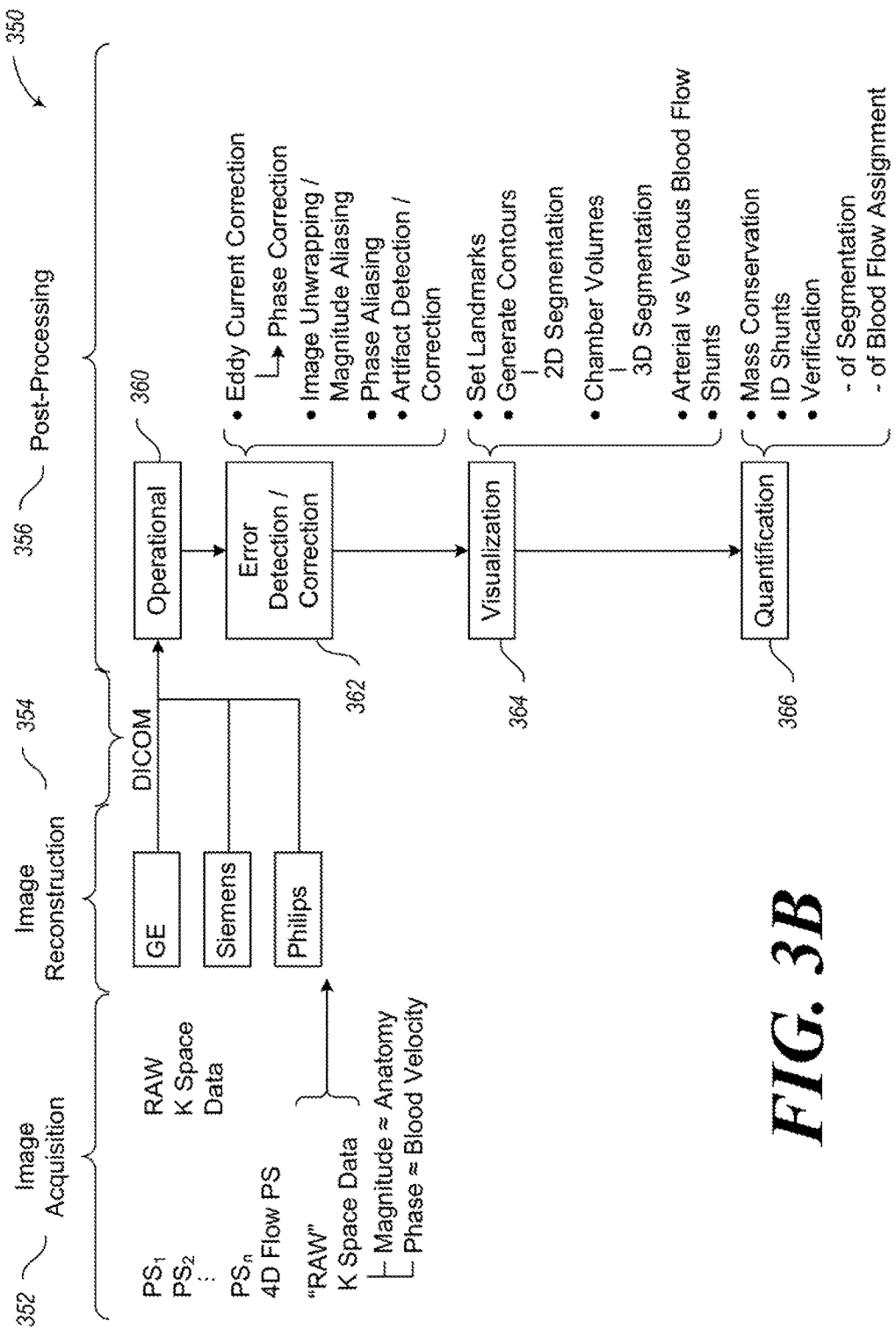
FIG. 3B is a schematic view of a data flow in an MRI imaging and processing/analysis environment, according to one illustrated embodiment.

FIG. 3B shows a data flow 350 in an MRI imaging and processing/analysis environment, according to one illustrated embodiment.

The MRI imaging and processing/analysis data flow 350 may be broken into three segments or phases, namely image acquisition phase 352, image reconstruction phase 354 and post-processing phase 356.

During the image acquisition phase 352, various pulse sequences ($PS_1$, $PS_2$, $PS_n$, 4D flow PS) are employed to drive the magnets of an MRI machine, and raw or K space MRI data or information is collected. The raw or K space MRI data or information may represent a plurality of voxels, and include magnitude values and phase values for each voxel. The magnitude values represent anatomical structures, while the phase values represent blood flow or velocity.

The raw MRI data is processed during the image reconstruction phase 354. The image reconstruction may, for example, result in standardized files, for example MRI data sets in the DICOM standard format. The image reconstruction may be specific to an MRI machine manufacturer, for instance GE, Siemens, and Philips, and may employ software or firmware provided by the MRI machine manufacturer. Typically, the image reconstruction is performed locally, at the site at which the MRI machine is located.

The MRI data sets (e.g., DICOM files) are further processed in the post-processing phase 356. In some particularly advantageous implementations, the post-processing phase 356 is performed remotely from the image acquisition phase 352 and image reconstruction phase 354. For example, the post-processing phase 356 may be performed at a dedicated post-processing facility, which may even be operated by an entity that is separate and independent from the entity or entities (e.g., clinical facility or organization) that perform the image acquisition phase 352 and image reconstruction phase 354.

The post-processing phase 356 may be divided into an operational phase 360, error detection and/or correction phase 362, visualization phase 364, and quantification phase 366. While sequentially illustrated, these phases 360-366 may be performed in a different order than illustrated, and may not be performed sequentially. For example, many of the actions grouped under each phase may be performed concurrently, or some acts in one phase may be performed before acts in another phase, while other acts in the one phase may be performed after acts in the other phase.

The operational phase 360 may include receiving requests (e.g., Web requests with MRI data sets), queuing requests, and providing responses. Many techniques are described below for implementing the operational phase, for instance via an asynchronous command and imaging pipeline architecture.

The error detection and/or correction phase 362 includes performing error detection on the MRI data set, and where possible error correction. The error detection and/or correction phase 362 may, for example, include performing eddy current detection and/or correction, phase detection and/or correction, image unwrapping, magnitude aliasing detection and/or correction, phase aliasing detection and/or correction, and/or artifact detection and/or correction. Many error detection and/or correction techniques are described in detail elsewhere herein. Many of the error correction and/or detection acts may be performed autonomously by a rendering or post-processing system, while others may employ human intervention or input to the computer.

The visualization phase 364 may include a variety of actions, for example defining or setting landmarks (e.g., anatomical landmarks or structures), generating two-dimensional contours and/or three-dimensional volumes, via segmentation. The visualization phase 364 may additionally include distinguishing between information representing arterial and venous blood flow, and identifying such, for instance via appropriate colors (e.g., blue(s), red(s)). The visualization phase 364 may additionally include identifying suspected shunts representing blood flow that should not occur in a healthy subject, and identifying such, for instance via appropriate colors. Many of the visualization acts may be performed autonomously by a rendering or post-processing system, while others may employ human intervention or input to the computer.

During the quantification phase 366 various characteristics may be quantized and compared. For example, the quantification phase 366 may employ the concept of mass conservation or flow conservation. Thus, flows of blood may be quantized and compared. For instance, a flow of blood into a volume should typically match the flow of blood out of the volume. The volume may, for example constitute a bodily organ, such as vasculature (e.g., artery, vein, sinus) or heart, chamber of the heart. The volume may be enclosed structure, with a natural inlet and a natural outlet. Alternatively, the volume may have a defined inlet and outlet which do not correspond to any naturally occurring entrance or exist. For instance, any segment of an artery may be delineated or identified as the volume. Also for instance, two or more anatomical structure may be combined to form or define the volume.

Comparing flow into and out of a volume may be used to identify shunt (e.g., defects allowing blood flow which should not occur in normal, healthy tissue). Comparing flow into and out of a volume may be used to validate or verify other post-processing actions, for example to validation segmentation or the assignment of arterial versus venous flow to one or more voxels.

Many quantification techniques are described in detail elsewhere herein. Many of the quantification acts may be performed autonomously by a rendering or post-processing system, while others may employ human intervention or input to the computer.

Pre-Acquisition

4D-Flow Localizer

A 4D-Flow localizer is a specific pulse sequence (i.e., instructions or drive signals which control the magnets of the MRI machine during an MRI scan or acquisition) that is tailored to gather information for a high fidelity 4D-Flow scan or acquisition. The 4D-flow localizer is essentially a first pass scan or acquisition to help prescribe appropriate or optimized settings for a second pass (i.e., high fidelity 4D-Flow scan or acquisition). Prior to the patient entering the scanner, the type of 4D-Flow localizer is selected based on the several variables. The clinical indication, type of contrast agent, amount of contrast agent, patient weight, patient height and heart rate, hardware manufacturer, type of cardiac coil used, and type of hardware (1.5 T or 3 T) will be used to predict the optimal localizer to use. The localizer data will then be sent to a processor-based system (e.g., server of the image processing and analysis system) to build a patient-specific 4D-Flow protocol.

Figures 4A, 4B:
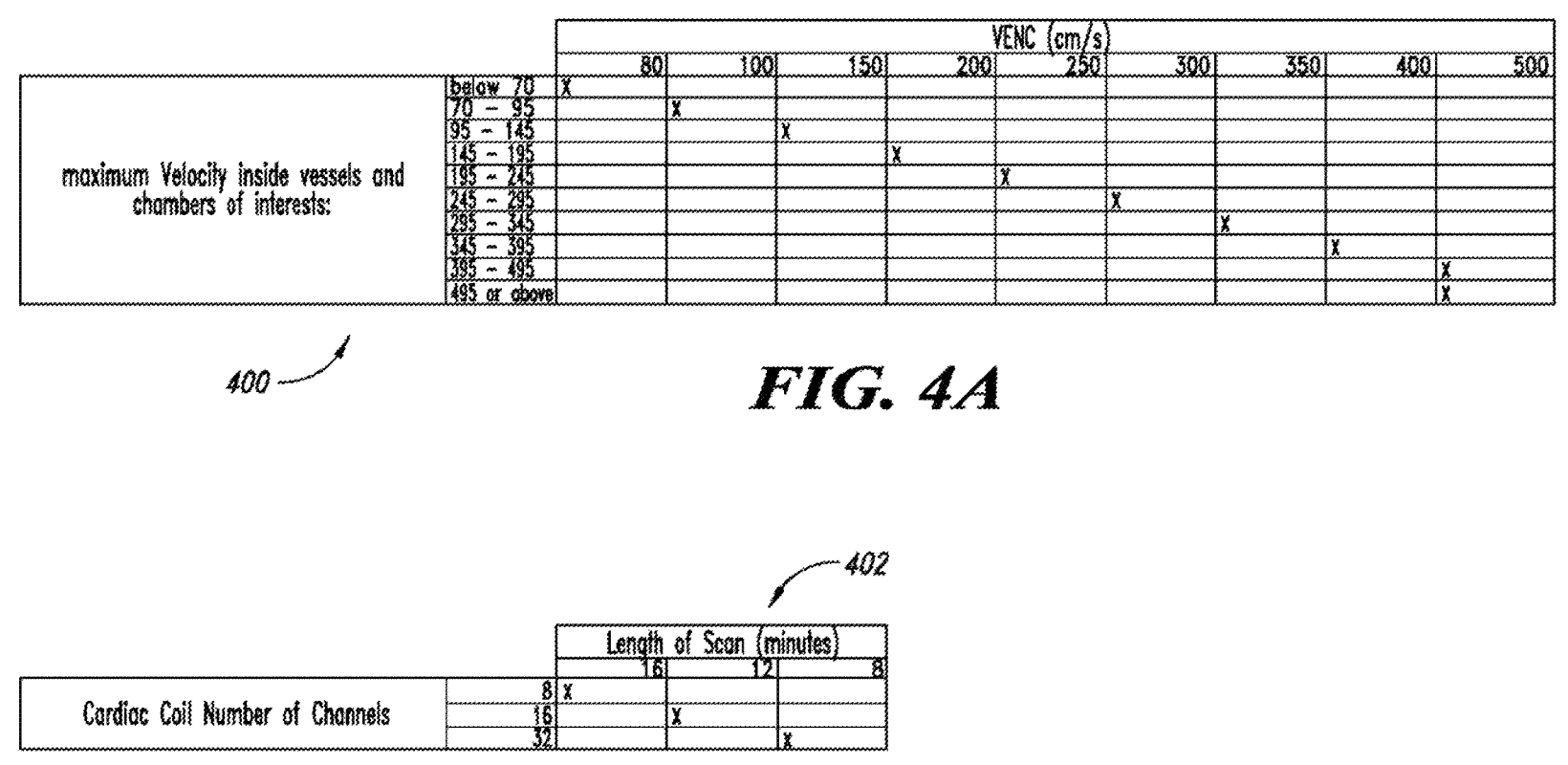

For example, the localizer may help to select the VENC (Velocity encoding) and required temporal resolution. For example, the VENC may be selected based wholly or in part on a maximum velocity found inside the vessel of interest. The VENC may be selected using a look-up table approach and/or interpolation. FIG. 4A shows a look-up table 400 with exemplary values of VENC for various ranges of velocity.

Also for example, a length or duration of a scan may be selected based wholly or in part on a number of channels of the coil (e.g., cardiac coil) being used for the MRI procedure. Typically, the lower the number of channels, the lower the signal to noise ratio (SNR), which means longer imaging times are required. FIG. 4B is a table 402 that shows a number of exemplary scan lengths or durations for a number of total channels for a cardiac coil.

In addition, as more data is collected and sent to servers of the image processing and analysis system, a learning or refinement algorithm can detect the optimal settings to use based on a set of input parameters. This algorithm could employ feedback from the clinician (e.g., from a range of 1-10 of the quality of the high-fidelity 4D-flow scan) to train the algorithm in knowing or recognizing whether the selected output variables were appropriate for a given scan (i.e., acquisition). The algorithm may employ one or more artificial intelligence (AI) techniques, including but not limited to training a neural network. life there are no training sets, default values of the input variables of the high fidelity 4D-Flow scan will be selected. Once the images come back to the server, in addition to a quality metric, this data is used in determining what the next scan settings should be. The goal is to increase the scan quality over time or number of procedures. The input parameters will be incremented or decremented to determine if scan quality increases or decreases. Once there are a sufficient number of training sets from a specific institution, a multi-variable optimization algorithm can be used to select the optimal input variables for any new patients that need to be imaged.

In use, for each patient the MRI imaging and analysis system may generate one or more pulse sequences which are patient specific, and which are used to operate the MRI machine to acquire MRI data sets. For example, the MRI imaging and analysis system may generate 4-6 pulse sequences for a patient. The MRI machine may execute the pulse sequences, for example in response to a single input by an MRI machine operator or technician. Notably, such allows capture or acquisition of the desired MRI data sets without requiring the attendance or time of a clinician (e.g., physician). Input may include patient characteristics, identification of a gradient coil, and/or contrast.

Figure 5:
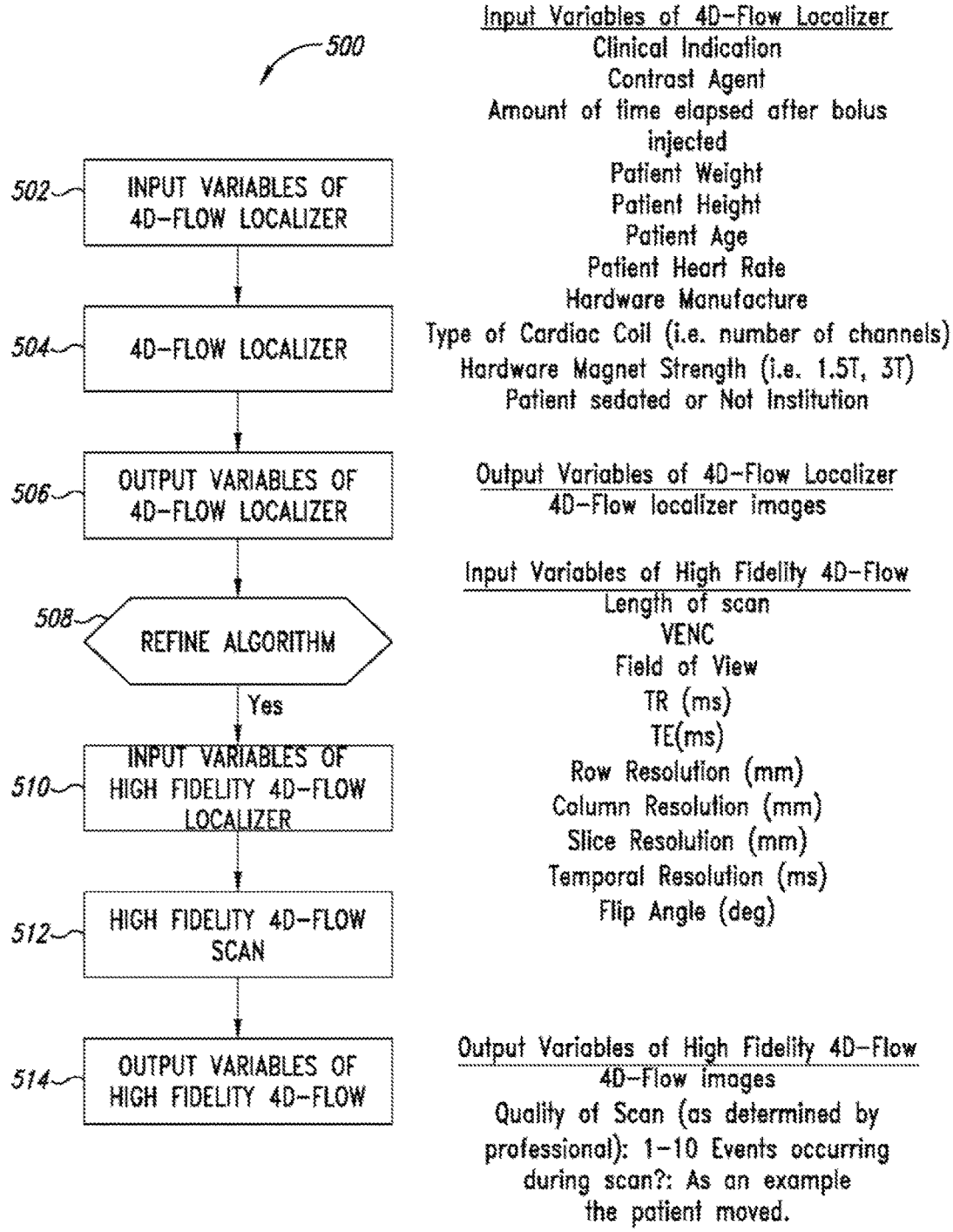
FIG. 5 is a flow diagram illustrating a method of operation with a 4D flow localizer and an optional refinement algorithm, according to one illustrated embodiment.

FIG. 5 illustrates a method of operation 500 with a 4D flow localizer and an optional refinement algorithm, according to one illustrated embodiment.

Initial input variables 502 are generated or collected to produce a 4D flow localizer 504. The input variables 502 may, for example, be collected via an MRI operator's system 112, for instance entered by a human and/or automatically or autonomously collected. Input variables 502 may include one or more of: clinical indication, name or identifier of contrast agent, amount or dosage of contrast agent, amount of time elapsed after bolus injected or provided to patient or subject, patient or subject weight, patient or subject height, patient or subject age, patient's or subject's heart rate, hardware manufacture, make, model, serial number or other hardware identifier, type of coil (e.g., cardiac coil, number of channels), hardware magnet strength (e.g., 1.5 T, 3 T), indication of whether patient or subject has been sedated or not, etc.

The 4D flow localizer 504 may be generated via a processor-based device. In many implementations the processor-based device will be part of the image processing and analysis system, although the teachings herein are not limited to such. For example, in some implementations the 4D-Flow localizer may be generated by a component or portion of the MRI acquisition system.

Operation of the MRI machine using the 4D flow localizer 504 generates or produces a set of output variables 506. The output variables 506 may, at least in some instances, take the form of 4D flow localizer images.

The output variables (e.g., 4D flow localizer images) are refined at 508. For example a processor-based device may execute an algorithm, for instance a machine learning algorithm. Alternatively, a neural network may be employed to perform the refinement.

As described above, a machine learning or other approach may allow refinement, generating a set of input variables of high fidelity 4D flow 510. The input variables of high fidelity 4D flow 510 may, for example, include one or more of: length or duration of scan or acquisition, VENC, field of view, repetition time (TR ms), echo time (TE ms), row resolution (mm), column resolution (mm), slice resolution (mm), temporal resolutions (ms), flip angle (degree).

A processor-based device uses input variables of high fidelity 4D flow 510 to generate a high fidelity 4D flow scan or acquisition 512. The high fidelity 4D flow scan or acquisition 512 results in output variables of high fidelity fl4D-Flow 514. The output of high fidelity 4D flow may, for example, include one or more of: 4D flow images, quality of scan (as assessed by one or more professionals, for instance on a scale such as 1-10), events occurring during a scan (e.g., patient moved).

Visualization

Arterial and Venous Blood Flow Isolation

In order to highlight the difference between left heart (i.e., arterial) or right heart (i.e., venous) blood flow, the MRI image processing and analysis system is operable to generate a unique color map (i.e., color gradient map) for each side. The MRI image processing and analysis system generates image data with voxels colored with a respective color map, either using 2D rendering or 3D rendering (i.e., pathlines and streamlines). Typically, arterial blood flow will have a red based color map and venous blood flow will have a blue based color map. With a healthy system these two blood pools never come in contact with each other, except at the microscopic level in the lungs for instance. In order to decide which voxel in a body belongs to which side, the MRI image processing and analysis system executes an algorithm that, for each voxel, detects or determines which bin the voxel belongs to, and assigns an appropriate color to that voxel.

Figure 6:
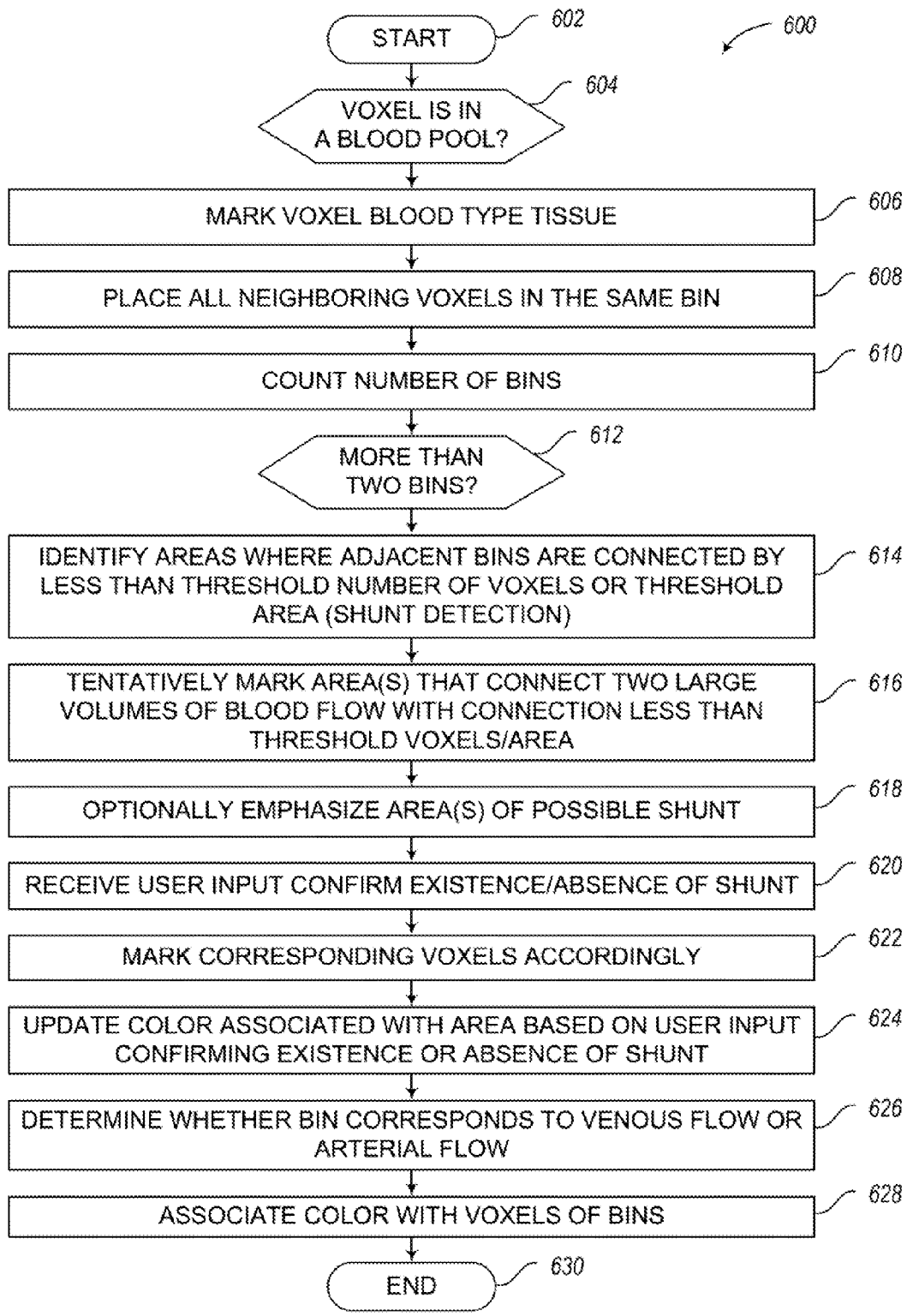
FIG. 6 is a flow diagram showing a high level method of operation of generating a color map of blood flow, according to one illustrated embodiment.

A method 600 of generating the color map of blood flow is illustrated in FIG. 6, according to one illustrated embodiment.

The method 600 starts at 602, for example in response to being called by a calling routine.

At 604, for each voxel of a plurality of voxels the MRI image processing and analysis system determines whether a given voxel is in a blood pool. To determine such, the MRI image processing and analysis system can employ any of a number of segmentation algorithms or methods, for example the various segmentation algorithms or methods described herein. The MRI image processing and analysis system may autonomously perform the segmentation and/or determination to identify an enclosed volume or area or pathway. Alternatively, the MRI image processing and analysis system may receive input from a human operator or user that identifies whether a given voxel is in the pool of blood or which otherwise facilitates segmentation between blood tissue and non-blood tissue. The determination may be repeated until, for example, all voxels have been analyzed.

At 606, if it is determined that the given voxel is in the blood pool, the MRI image processing and analysis system marks (e.g., logically), identifies or otherwise logically assigns the given voxel as blood type tissue.

At 608, the MRI image processing and analysis system places all neighboring voxels which have been marked or identified as blood in the same bin. If these bins spatially come in contact with each other over time, the MRI image processing and analysis system consolidates the contacting bins of voxels in the same bin. Optionally, the MRI image processing and analysis system may compute streamlines and/or pathlines in the blood pool, which could highlight which bins are connected.

At 610, the MRI image processing and analysis system counts the number of bins. Ideally there will be only two bins, one corresponding to arterial blood flow and one to venous blood flow.

At 612, the MRI image processing and analysis system determines whether there are more than two bins. If the MRI image processing and analysis system determines that there are more than two bins, control passes to 614. Otherwise control passes to 626.

Areas where there is a shunt (i.e., connection between the left and right heart flow), are typically indicative of a medical problem or abnormal condition. As indicated at 614, the MRI image processing and analysis system may perform a shunt detection method or algorithm on these areas. A suitable shunt detection method or algorithm is described elsewhere herein. For example, the MRI image processing and analysis system may determine or identify areas where adjacent bins are connected by a number of voxels that is less than a defined threshold number of voxels or a defined threshold area. For example, if the threshold is 10 voxels, the MRI image processing and analysis system may tentatively mark or identify any area that connects two large volumes of blood flow together with less than 10 voxels as a shunt as illustrated at 616. Care must be taken to not assume such areas are necessarily shunts. These areas could, for example, be a stenotic valve or stenosis. Optionally at 618, the MRI image processing and analysis system visually emphasizes (e.g., highlights) these areas for the operator or user. The operator or user could very quickly visually confirm the existence or absence of a shunt, and provides a corresponding input which is received by the MRI image processing and analysis system as indicated at 620. At 622, the MRI image processing and analysis system marks or identifies the corresponding voxels accordingly. At 624, the MRI image processing and analysis system updates or assigning a color associated with the area based on the user input confirming the existence or absence of a shunt. For instance, if existence of a shunt is confirmed, the MRI image processing and analysis system will color the corresponding area with neither the red nor blue color map. Instead, the MRI image processing and analysis system may associate a unique color with this area of voxels to visually emphasize (e.g., highlight) this area for the operator or user.

At 626, the MRI image processing and analysis system determines whether a bin corresponds to venous flow or arterial flow. Various approaches to determining whether a bin corresponds to venous flow or arterial flow are discussed herein with reference to FIGS. 4 and 5 At 628, the MRI image processing and analysis system associates the voxels of each of the two bins with a respective color or set of colors, for instance blue or blues for arterial and red or reds for venous flow. The method 600 terminates at 630.

Figure 7:
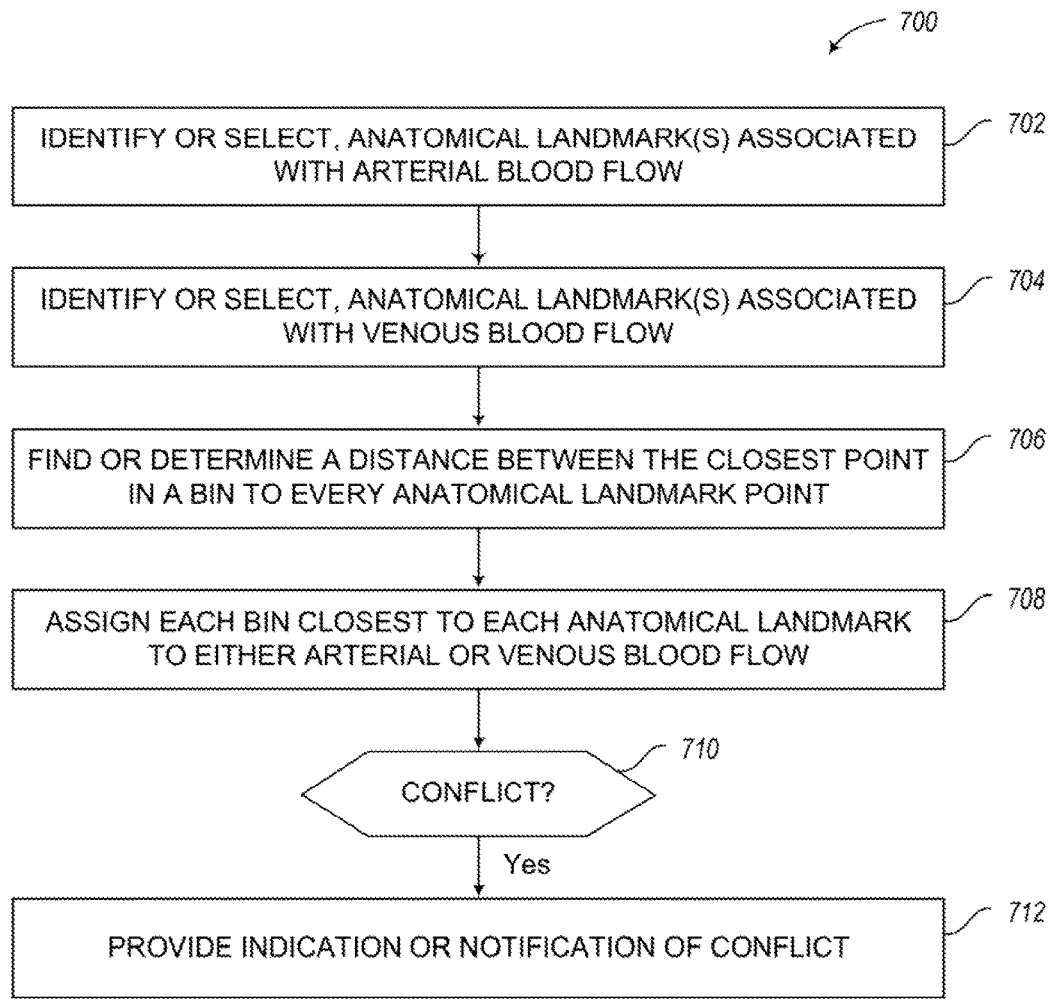
FIG. 7 is a flow diagram showing a method of determining whether a bin corresponds to venous flow or arterial flow, according to one illustrated embodiment.

FIG. 7 shows a method 700 of determining whether a bin corresponds to venous flow or arterial flow, according to one illustrated embodiment. The method 700 is particularly suitable if anatomical landmarks (i.e., point in space, e.g., apex of left ventricle) have already been defined, allowing simple selection of just the landmarks that are within the blood pool. Techniques for identification and/or selection of landmarks are described elsewhere herein.

To define arterial blood flow, at 702 the MRI image processing and analysis system may autonomously identify or select, or may receive user input from manual identification or selection of one or more of anatomical landmarks associated with arterial blood flow. The anatomical landmarks may, for example, include one or more of an aortic valve point, a mitral valve point, and/or an aorta (e.g., point in the aortic sinus, point in the ascending aorta, point at the top of the aortic arch, point in the descending aorta).

To define venous blood flow, at 704 the MRI image processing and analysis system may autonomously identify or select, or may receive user input from manual identification or selection of one or more of anatomical landmarks associated with venous blood flow. The anatomical landmarks may, for example, include one or more of a pulmonary valve point, a tricuspid valve point, a point in a left pulmonary artery, a point in a right pulmonary artery, a point in inferior vena cava, and/or a point in superior vena cava.

At 706, the MRI image processing and analysis system may autonomously find or determine a distance between the closest point in a bin to every anatomical landmark point. Ideally this distance should be zero because each landmark is in a respective one of the blood pools. At 708, the MRI image processing and analysis system assigns each bin closest to each anatomical landmark to either arterial or venous blood flow, depending on whether the anatomical landmark is in the arterial or venous blood pool. At 710, the MRI image processing and analysis system determines whether there is conflict. A conflict indicates either the existence of a shunt, or that a connected group of voxels are in the wrong bin. In response to identification of a conflict, the MRI image processing and analysis system provides an indication or notification at 712.

The MRI image processing and analysis system implements image navigation, for instance autonomously or in response to operator or user input. For example, the MRI image processing and analysis system implements distance scrolling, allow movement through a defined number of spatial slices is some defined spatial direction (e.g., along X axis, y axis or z axis) and comparison of data between the spatial slices. For example, the MRI image processing and analysis system implements time or temporal scrolling, allow movement through a defined number of temporally sequential slices is some defined temporal direction (e.g., increasing time, decreasing time) and comparison of data between the temporal slices. As noted elsewhere herein, the MRI image processing and analysis system may advantageously use the comparison between slices employed to identify artifacts. For example, the MRI image processing and analysis system implements zoom and/or pan operations, allowing an operator or user to zoom in on portions of an image or pan across an image.

Figure 8:
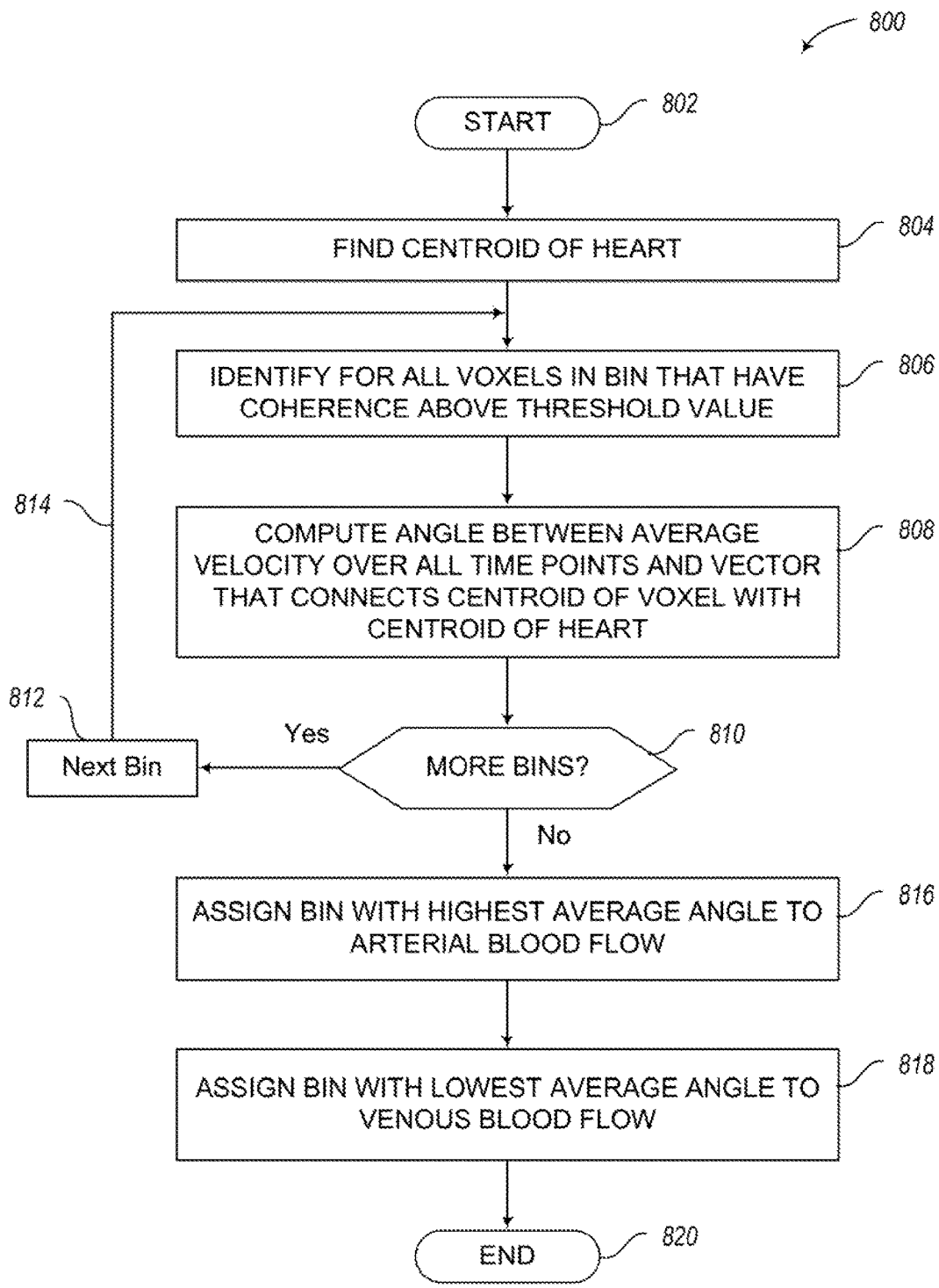
FIG. 8 is a flow diagram showing a method of determining whether a bin corresponds to venous flow or arterial flow, according to one illustrated embodiment.

FIG. 8 shows a method 800 of determining whether a bin corresponds to venous flow or arterial flow, according to one illustrated embodiment. The method 800 is particularly suitable if anatomical landmarks have not be identified.

The method 800 is starts at 802, for example in response to a call from a calling routine.

The method 800 is based on Vector Angles. At 804, the MRI image processing and analysis system finds the centroid of the heart. Such may be performed autonomously or may be based on operator or user input. For example, the centroid can actually be extracted from the DICOM tags since there is a patient coordinate system in these fields and where 0,0,0 corresponds to a specific point in the patients anatomy.

At 806, the MRI image processing and analysis system determines or identifies for all voxels in a bin that have coherence above a threshold value. At 808, for all voxels in a bin that have coherence above a threshold value, the MRI image processing and analysis system computes the angle between the average velocity over all time points and the vector that connects the centroid of the voxel with the centroid of the heart. The MRI image processing and analysis system then computes the average angle between all voxels in a bin and the centroid. At 810, the MRI image processing and analysis system determines if there are additional bins to processor, incrementing the bin at 812 in a loop 814 to repeat the computations 806, 808 for all bins. Since arterial blood flow moves away from the heart, the MRI image processing and analysis system assigns the bin that has the highest average angle to be arterial blood flow at 816. The MRI image processing and analysis system assigns the bin that has the lowest average angle to be venous blood flow at 818.

The method 800 terminates at 820.

Additionally or alternatively, the MRI image processing and analysis system may employ probability. Based on several other datasets where the blood pool has already been identified, the MRI image processing and analysis system can create an atlas and then compared a new dataset with the atlas. By co-registering the atlas and new dataset, the MRI image processing and analysis system can assign the bin the correct blood pool.

Additionally or alternatively, the MRI image processing and analysis system may employ velocity signals. Notably, the blood velocity waveform of a vein is unique with respect to the blood velocity waveform of an artery (e.g. lower speed flow, and shape of the waveform is unique).

Blood Flow Filter Based on Directional Coherence

A filter may be used to isolate blood flow voxels by measuring directional coherence.

The filter may be a 4D feature extraction operator that determines how similar a 3D flow vector at a particular voxel is compared to the flow vectors of its neighboring voxels. The filter may determine how similar a 3D flow vector at a particular voxel at a given time is with the 3D flow vector of the same voxel at time points before and after the given time. This may assist in filtering out random noise, resulting in isolating blood vessels.

The filter can be generated in one volume per time point, to allow moving blood vessels. Alternatively, the filter can be generated as one volume which is averaged over all time points, which is typically achieves better noise reduction by itself. The averaging period could be changed from the cine's length (i.e., duration of resulting acquisition) to a cardiac or respiratory phase.

The filter can be assisted with another filter to further remove random noise, such as (anatomy_magnitude*velocity_magnitude) with a Boolean or weighted function.

Since both filters only rely on a single input each (e.g., percentage threshold), the filters can be combined into a single 2D input gesture. An example would be where moving from left to right increases the directional coherence percentage threshold, and moving from the bottom to the top increases the second filter's percentage threshold.

Since quality/magnitude of velocity volumes varies from anatomy sections, sites, scanners, etc., different default values for these filters could be used per metadata combinations.

The directional coherence for a particular voxel is calculated by: summating the weighted directional coherence scores between the voxel and all applicable neighboring voxels, and dividing by the summation of all of the weights that were applied. For example, if a voxel were on the left edge of a volume, the applicable neighboring voxels would consist of all voxels within a given radius to all dimensions except the left, as well as the same center voxel on adjacent time point volumes.

The directional coherence score between two voxels is calculated by: taking the dot product of the normalized velocity vectors, running those through the function ACOS to get the angled difference, and then scaling that angle between 0-Pi to get a 0-1 result. That result is then multiplied by a weight (signifying the distance between the voxels). If one of the voxels has a velocity with magnitude 0, then a default score of 0.5 is multiplied by the weight.

The weight applied to a directional coherence score is calculated by: finding the minimum spacing for all three dimensions, and dividing that number by the distance between the voxels (as defined by the spacing). For example, the "weight" for a voxel on the adjacent slice, a column over and a row up would be: min_spacing/sqrt(column_spacing$^2$+row_spacing$^2$+slice_spacing$^2$).

After all directional coherence scores are calculated, the min and max values are found and used to scale the scores inside a given range for more effective thresholding.

Quantification

Result Validation

There are physical principles that provide insight into whether flow data is correct. For example, flow entering an enclosed volume must equal flow exiting the enclosed volume. A mismatch between the flow values entering and exiting an enclosed volume may be indicative of a shunt or other anatomical problem. The MRI image processing and analysis system may employ this general principal in a variety of specific ways. Such may, for example, be determined as the dot product of a normal vector of a plane that slices a volume and a velocity vector at each point or voxel. For net flow, the dot product may be integrated over time. The flow may, for instance be represented as pressure per time (e.g., millibars per second) or as volume per time (e.g., liters per second).

i) Flow entering a closed vessel or portion thereof must match the flow exiting a closed vessel. The MRI image processing and analysis system can autonomously identify, or be used by a human operator to identify vessels or lumens or other delineated volumes or cavities of various organs, and then identify inlets and outlets of vessels or lumens or delineated volumes. The inlets and/or outlets may be anatomically significant starts or ends of a lumen or physical port or opening. Alternatively, the inlets and/or outlets may be logical constructs, for example defined spaced inwardly of natural starts, ends or openings or ports. The MRI image processing and analysis system can autonomously determine whether the flow value at the inlet matches the flow value at outlet, for example within some defined threshold (e.g., 1%). The MRI image processing and analysis system can provide an indication of the result of the determination. For example, MRI image processing and analysis system can provide an indication that the flow does not match, an indication of an amount or percentage of mismatch, and/or an indication that the flow matches.

ii) Flow through the Ascending Thoracic Aorta should match the combined flow of through the Superior Vena Cava (SVC) and the Descending Thoracic Aorta. The MRI image processing and analysis system can autonomously identify, or be used by a human operator to identify the Ascending Thoracic Aorta, the SVC and the Descending Thoracic Aorta. The MRI image processing and analysis system can autonomously determine whether the flow value through the Ascending Thoracic Aorta match the combined flow of through the SVC and the Descending Thoracic Aorta, within some defined threshold (e.g., 1%). The MRI image processing and analysis system can provide an indication of the result of the determination. For example, MRI image processing and analysis system can provide an indication that the flow does not match, an indication of an amount or percentage of mismatch, and/or an indication that the flow matches.

iii) Combined flow through the SVC and the Inferior Vena Cava (IVC) should match flow through the Pulmonary Vasculature (PA). The MRI image processing and analysis system can autonomously identify, or be used by a human operator to identify the SVC, IVC, and PA. The MRI image processing and analysis system can autonomously determine whether the combined flow value through the SVC and IVC matches the flow through the PA, within some defined threshold (e.g., 1%). The MRI image processing and analysis system can provide an indication of the result of the determination. For example, MRI image processing and analysis system can provide an indication that the flow does not match, an indication of an amount or percentage of mismatch, and/or an indication that the flow matches.

iv) The flow through the PA should match the combined flow through the Right Pulmonary Vasculature (RPA) and the Left Pulmonary Vasculature (LPA). The MRI image processing and analysis system can autonomously identify, or be used by a human operator to identify the PA, RPA, and LPA. The MRI image processing and analysis system can autonomously determine whether the flow value through the PA matches the combined flow value through the RPA and LPA, within some defined threshold (e.g., 1%). The MRI image processing and analysis system can provide an indication of the result of the determination. For example, MRI image processing and analysis system can provide an indication that the flow does not match, an indication of an amount or percentage of mismatch, and/or an indication that the flow matches.

v) The flow through the LPA should match the sum of flow through all left pulmonary veins. The MRI image processing and analysis system can autonomously identify, or be used by a human operator to identify the LPA and left pulmonary veins. The MRI image processing and analysis system can autonomously determine whether the flow value through the LPA matches the flow through all left pulmonary veins, within some defined threshold (e.g., 1%). The MRI image processing and analysis system can provide an indication of the result of the determination. For example, MRI image processing and analysis system can provide an indication that the flow does not match, an indication of an amount or percentage of mismatch, and/or an indication that the flow matches.

vi) The flow through the RPA should match the sum of flow through all right pulmonary veins. The MRI image processing and analysis system can autonomously identify, or be used by a human operator to identify the RPA and right pulmonary veins. The MRI image processing and analysis system can autonomously determine whether the flow value through the RPA matches the flow through all right pulmonary veins, within some defined threshold (e.g., 1%). The MRI image processing and analysis system can provide an indication of the result of the determination. For example, MRI image processing and analysis system can provide an indication that the flow does not match, an indication of an amount or percentage of mismatch, and/or an indication that the flow matches.

vii) The flow through a closed volume should be the same without regard to an orientation of a plane that cuts the closed volume. The MRI image processing and analysis system can autonomously identify, or be used by a human operator to identify, two or more planes that intersect a given point and which each cut across a vessel at a respective orientation (i.e., two or more planes with different normal vectors that each intersect a same point). The MRI image processing and analysis system can autonomously determine whether the flow over the full cardiac cycle match for all of the planes, at least within some defined threshold. The MRI image processing and analysis system can provide an indication of the result of the determination. For example, MRI image processing and analysis system can provide an indication that the flow does not match, an indication of an amount or percentage of mismatch, and/or an indication that the flow matches.

viii) A flow existing a cardiac chamber of a heart should match a change in systolic and diastolic volume for each cardiac chamber of the heart. The MRI image processing and analysis system can autonomously identify, or be used by a human operator to identify one or more chambers of a heart. The MRI image processing and analysis system can autonomously determine. The MRI image processing and analysis system can provide an indication of the result of the determination. For example, MRI image processing and analysis system can provide an indication that the flow does not match, an indication of an amount or percentage of mismatch, and/or an indication that the flow matches.

The MRI image processing and analysis system may perform any one or more of the above operations as validation of results, either manually or autonomously. This can provide a confidence measure, indicative of the accuracy of the flow values. For example, instead of just providing (e.g., displaying) a flow value (e.g., 5.4 L/min), the result validation allows the MRI image processing and analysis system to provide the results with an indication of accuracy (e.g., 5.4 L/min±0.3 L/min. with a 95% confidence interval. An error estimate can be determined by evaluating a difference between the left and right sides of the relationships listed above. In addition, other error estimates can be derived by perturbing the measurement several times (e.g., in position, orientation, and dilation/erosion of contour), thereby generating several measurements that can be statistically evaluated (e.g., average, 95% confidence interval, etc.). Knowing the level of possible error in the data or results also can help other pre-processing algorithms (i.e., eddy current correction). For example, this may be used by the implementing algorithms to know in which direction to skew the data to make the data or results more accurate.

Segmentation

Flow Driven Segmentation

Various implementations described herein advantageously employ blood flow datasets (i.e., x velocity, y velocity, and z velocity) as input for any type of quantification. Conventionally, only anatomic (i.e., magnitude) datasets have been used for magnetic resonance (MR) quantification. As an example, a blood flow dataset can serve as a proxy for blood flow quantification, but also can be used as input for determining a luminal border of a vessel or chamber (i.e., segmenting the anatomic dataset). The blood flow dataset can also be used for computing pressure, wall shear stress, as well as determining how to render 2D and 3D images. As an example of how flow can alter the rendering of an image: the MRI image processing and analysis system may render only anatomic voxels that match a certain flow condition (i.e., if the velocity magnitude in that voxel is above a certain defined threshold, for instance a user defined threshold).

An example is flow driven segmentation (e.g., volume, area, pathway) to isolate blood from other tissue types. As a specific example, volumetric segmentations of the chambers of the heart. Some of the time points in the scan may have a very high magnitude for flow in the chambers of the heart. The MRI image processing and analysis system may use these time points to derive a geometric model of a chamber. Once the geometric model has been derived from the high flow magnitude time points, the MRI image processing and analysis system can coregistered the model with the magnitude scan. The MRI image processing and analysis system may subsequently register the model with the other time points to find the non-linear transforms that line up the model with the other time points.

In an exemplary algorithm for segmenting a blood vessel and determining a luminal border of a vessel cross section is provided, given a seed point in a vessel, the time point with the highest flow magnitude at the seed point is identified. This time point denotes when the strongest jet of blood is moving through the vessel. The system uses a combination of the anatomy and velocity data in order to determine the cross section that is perpendicular to the direction of flow. The direction of flow gives a strong indication of the cross section normal to use. In some cases, the flow may have turbulence which would lead to a poor result. Additionally, the system make take a coarse hemisphere of vectors at the seed point, where vectors closest to the flow direction have the highest weight. For each of the vectors that make up the hemisphere, several rays are cast perpendicular to the vector on the hemisphere. These rays are terminated when the magnitude of the change in both anatomy pixel intensity and velocity magnitude has changed sufficiently. This provides an approximation of the boundary of the vessel on that plane. The seed point, the termination of ray n, and the termination of ray (n+1) from a triangle. The system computes the sum of areas of all the resulting triangles. The vector on the hemisphere that has the smallest result area from this computation is selected as the normal for the plane that is most perpendicular to the direction of flow.

Next a multi-planar reconstruction (MPR) is resampled combining (i.e. product) both the anatomy and velocity data at the initial seed point, the strongest flow time point, and with the normal vector from the previous step. A technique called active contour model or snakes may be used to find the contour that outlines the luminal border of the vessel. A seed contour is created based on the termination points of the rays that were cast to find the area measurement. The active contour then attempts to find a smooth contour that outlines the vessel wall. This smooth contour is found by applying an energy minimization function using gradient descent. The forces involved in the energy function include: 1) internal forces of the first and second derivatives using finite differences for points on the contour; 2) an external force that is constantly pushing outward from the centroid (balloon force); and 3) an external force that pulls points toward areas with a large gradient magnitude.

The internal forces ensure that the contour will be smooth. The outward pushing force is used to expand the contour through the MPR. The force pulling towards large gradient magnitudes should overcome the balloon and gravitate the contour to the vessel wall. Since the algorithm that is determining the luminal border of the vessel is heavily influenced by gradients within the MPR, the MPR is first smoothed, for instance using Gaussian convolution. Once the contour for the strongest flow time point has been found, the remaining time points are evaluated in the same way. Since the active contour model can be very sensitive, if a contour diverges sufficiently in area or curvature, it is treated as thrown out. Any contours that have been thrown out are replaced with a contour that is a linear blend of contours from adjacent time points.

Overall Process

Asynchronous Command and Imaging Pipeline.

Commands are sent from the client to the server using a persistent connection over a Web socket protocol. Images are returned through standard over the same Web socket connection. Since user events can happen with significantly higher frequency than the application is able to generate images and return them to the client some events must be squelched. Using an asynchronous command and image pipeline allows every important user event to be sent to or handled by, the server. All important events are captured to persistence layer and decide, allowing time, if needed, to determine which events will be squelched, if any, to create the best possible user experience. Images will only be processed and returned to the client at the rate the network is capable.

The architectural design for a remotely located rendering system (i.e., image processing and analysis system) involves commands being sent from a client to a Web server, the Web server interpreting these commands, and one or more compute servers generating images or computational results to be sent back to the client, for instance via the Web server. If the message involves work that can be distributed, multiple compute nodes may be used, otherwise the message will be routed to the appropriate compute node. The problem with a simplistic design where every user event generates an image or computation is that user events can occur with significantly higher frequency than the rendering system is able to generate results and have the results returned to the client over a network by the server. Also, simply squelching events can result is important user interactions being missed.

The network may employ an asynchronous command and imaging pipeline, which uses two communication channels, one for the client to send commands to the server, and one for the server to send responses to the client. This approach allows the capture of all events to a persistence layer, and to intelligently decide which events will be squelched, and conversely which events will be serviced, to create the best possible user experience. Results will only be processed and returned to the client at the rate the image processing and analysis computation can be performed and transmitted.

Figure 9A:
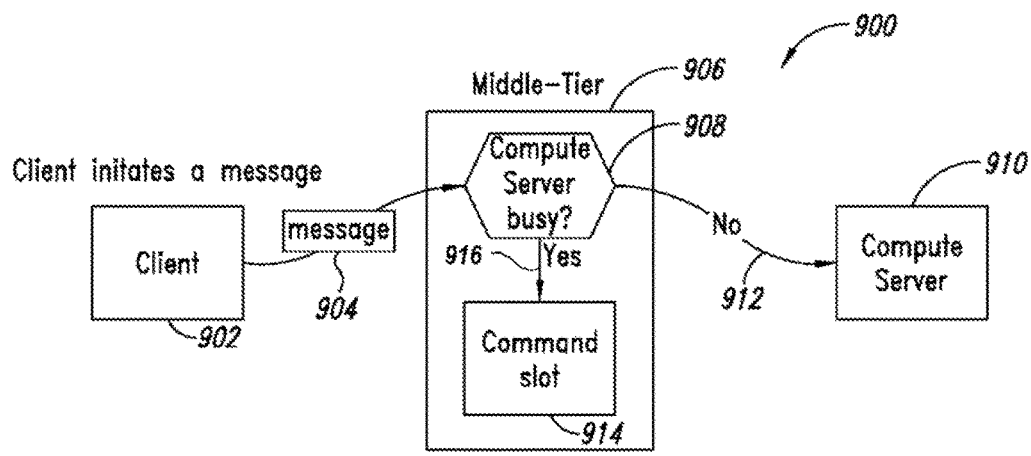
FIG. 9A is schematic diagram of operation of an asynchronous command and imaging pipeline, according to one illustrated embodiment.
Figure 9B:
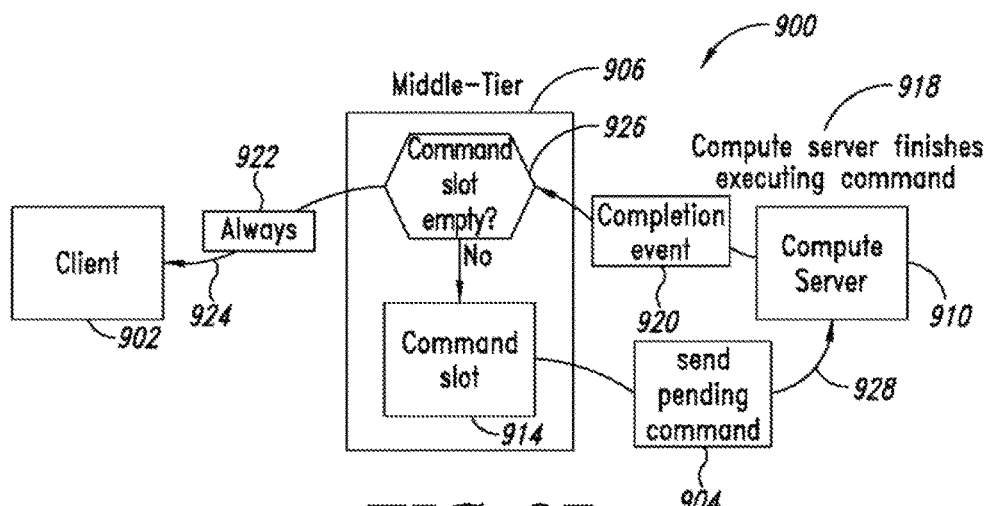
FIG. 9B is schematic diagram of operation of the asynchronous command and imaging pipeline of FIG. 9A, at a different time.

An example of operation of the asynchronous command and imaging pipeline 900 is illustrated in FIGS. 9A and 9B. As illustrated in FIG. 9A, a client 902 initiates a message 904. A middle-tier 906 receives the message 904 and determines which compute server will handle the message. At 908, the middle-tier 906 checks to determine if the compute server 910 (e.g., server of image processing and analysis system 104 of FIG. 1) is already busy executing an equivalent command. If the compute server 910 is not busy, the message 904 is immediately forwarded to the compute server 910 as illustrated by arrow 912. Otherwise the message 910 is placed in a command slot 914, as illustrated by arrow 916, to be executed upon receiving the completion event from the compute server 910. If another message 904 arrives before the compute server 910 is ready, the message in the command slot 914 is replaced with the newer one. Alternatively, newer messages may be added in a queue.

As illustrated in FIG. 9B, when the compute server 910 has finished executing the command 918, the compute server 910 raises a completion event 920. The Middle Tier 906 receives the completion event 920 and forwards the response 922 as indicated by arrow 924 to the client 902.

The Middle Tier 906 determines if there is a message in the command slot 914 at 926. If there is a message in the command slot 914, the when the completion event 920 fires the Middle Tier 906 sends the message 904' to the compute server 910 as indicated by arrow 928, and the command slot 914 is cleared.

As another example of a suitable imaging pipeline, some workflows require multiple images to be rendered at the same time that have linked properties. In some cases, the current workflow act may require simultaneous viewing of, for instance 20 images. If each of these images was retrieved with a distinct request, performance would suffer greatly as there is significant overhead in creating and sending a request. Instead, all the images may be rendered onto or as one large image, and only a single response for that resulting 'sprite sheet' is sent. The client then displays the images by using pixel offsets. For example, if a view had four images each 256×256, the sprite sheet might be 256×1024 with each of the images placed or arranged one on top of another. The client would then display 4 images at 256×256 by using offsets of 0, 256, 512, and 768.

In addition, any lines, markers, or planes in the images are drawn on the client as an overlay, and the information that informs the client how to render the overlay comes from the server via a text based message. This provides higher quality rendering of the overlay data than if the overlay were to be rendered on the server and then encoded as a JPEG and transmitted.

Workflow Architecture

Description: One of the primary advantages of 4D-Flow, is that during acquisition there is no need to have a radiologist on-site. A technician just needs to locate the chest or area of interest, and then press one button to start acquiring this area of interest. This drastically changes the typical cardiac MR workflow. In addition, due to the off-line processing, the patient can immediately leave the scanner after the acquisition. If a technologist is concerned with image quality, perhaps because the patient moved during acquisition, accelerated reconstruction can be used to give back 1 cardiac phase of images to the technician with 5 minutes or less. Once the technician has verified that quality of the images, they can feel confident in letting the patient leave. Once the full 4D-Flow scan has been completed the raw data is sent for automated image reconstruction (this can be done online at the scanner or off-line). If this is done off-line, this can be done in the hospital network or in the Morpheus cloud. After image reconstruction the workflow is to take the DICOM images and import them into the Morpheus software. At this point a Morpheus technician or hospital technician goes through the workflow steps highlighted above (image pre-processing, segmentation, visualization, and quantification) to process the case off-line. The goal is to set up the case for the clinician such that when the clinician sits down in front of the Morpheus software all they need to do is validate and annotate the report. The goal is to have this process completed in 10 minutes or less. This workflow is drastically different than many other software applications on the market today primarily because very few software applications are connected to a central database (i.e. in the cloud) and have the flexibility to allow multiple users to quickly access the data on any device (e.g. laptop at home, tablet, etc.).

Anonymization Service

There are numerous regulatory requirements for a class of information typically denominated as protected health information (PHI). Many clinical facilities (e.g., hospitals) or entities that operate clinical facilities do not want any PHI to leave their network or control. Likewise, to avoid onerous handling and security requirements and to eliminate or reduce potential liability, an entity that provides services to the clinical facility may desire to be isolated from PHI. Various implementations of the networked environment may implement a service that prevents PHI from ever leaving the clinical facility's own network.

A number of approaches are described herein, the preferred approach depending on a location of a database that holds the PHI.

In cases where the database containing PHI and the computer nodes which require access to the PHI are all within the clinical facility's own network there are typically two different implementations that allow a user to access the MRI imaging and analysis services provided by a remotely located MRI image processing and analysis system which is outside the clinical facility's own network.

1) A first implementation employs multiple firewalls. Clinical facility (e.g. Hospital) deployment should consist of several security layers. The secure clinical facility network should contain all PHI information (e.g., MONGO® database, data files). The MRI image processing and analysis system (e.g., server component thereof) should run in a demilitarized zone (DMZ) or perimeter network configuration, with appropriate access permissions to the secure clinical facility network for data access as required through a firewall. Another firewall should separate the DMZ from the Internet, and only ports 80 and 443 should be exposed to the public through the Internet. This way a user can login via a regular URL from a remote location or network (e.g., home), and access (e.g., see) PHI from the remote location or network.

2) A second implementation employs a virtual private network (VPN). The particular URL for accessing the services provided by the MRI image processing and analysis system is only accessible if the client device is first connected through a VPN of the clinical facility.

In cases where the clinical facility does not want the PHI in databases outside clinical facility's own network and the computer nodes which require access to the PHI are hosted outside the clinical facility's own network (e.g., AMAZON® Web Services or AWS), an anonymization service can run within the clinical facility's network. The anonymization service receives raw DICOM files, anonymizing the raw DICOM files by removing any plain text PHI, and replaces the plain text PHI with a hash of the PHI (e.g. all PHI fields in the DICOM images are identified and converted to salted hashes). A key that turns the plain text PHI into a hash is kept within the clinical facility's own network and is accessible by the anonymization service.

This anonymization service can operate in at least two ways

1) A first implementation employs a Proxy Server. As requests come from a client, either within the clinical facility's network or outside the clinical facility's network, the request passes through a proxy server, and the anonymization service replaces the hash with the plain text PHI. This allows the client to always see PHI. In this implementation, all HTTP/S requests are funneled to the proxy server.

2) A second implementation employs a one-time Lookup. When a client connects to the server(s) of the MRI image processing and analysis system, which are located outside the clinical facility's network, a flag indicates to the client whether the client is missing information required to render the PHI. If the client does not have the plain text PHI, the client connects to the anonymization service and requests the PHI by providing the hash or an identifier (ID). The correct plain text PHI is then provided to the client based on that provided hash or ID. The received PHI is then stored locally (cached) by the client, as long as the session is active. When the user logs out, the client purges the cache.

In all of the above described implementations, PHI is transmitted from the client to/from the anonymization service to/from server encrypted. In addition, any stored data may also be in encrypted form.

In the case that a customer would want their PHI hosted in the cloud, but in some circumstances wants to hide PHI in their client (e.g. for academic conferences) we have created an anonymization filter (which will be part of the anonymization service). The anonymization filter is a filter that is installed on the client data stream that inspects the traffic that passes through the filter and removes PHI before allowing data to proceed through the communication pipeline (it's a streaming data filter).

Phase Aliasing Detection and/or Correction

Phase aliasing is typically the result of a 27 offset of certain information in the MRI data set. Phase aliasing may, for example, appear as a voxel of wrong color, for example the appearance of a black voxel representing a blood flow in a first direction, where immediately adjacent voxels are white representing a second direction, for instance opposite the first direction. Phase aliasing may be the result of the velocity encoding (VENC) parameter being set incorrectly (e.g., too high). Notably, it is generally desirable to set the VENC parameter high to achieve better resolution, however setting the VENC parameter too high will tend to cause voxels to appear as a "negative" image.

To detect such, the MRI image processing and analysis system may detect a body of an anatomical structure, for instance a vessel. The MRI image processing and analysis system may then analyze each voxel within the detected boundary, determining flow within the bounded volume is all in a same direction or within a defined angular threshold of the same direction. In particular, the MRI image processing and analysis system may compare a respective vector for each of the voxels, the vector indicative of a direction of movement of the tissue represented by the particular voxel. The MRI image processing and analysis system may mark voxels that appear to be aberrant. The MRI image processing and analysis system may check neighboring voxels, for example nearest neighbors, and/or next nearest neighbors outward to some defined extent or degree. For instance, the MRI image processing and analysis system may initially check the nearest neighbors to a given voxel, in either two-dimensions or more typically three-dimensions. In response to identifying one or more apparently aberrant neighboring voxel, the MRI image processing and analysis system may iterate outwardly to a next level of voxels. This may include all next nearest neighboring voxels to the first apparently aberrant voxel, or the nearest neighboring voxels to the second, or later identified apparently aberrant voxels. The MRI image processing and analysis system defines or forms a region of interest (ROI) from the set of apparently aberrant voxels.

Additionally or alternatively, the MRI image processing and analysis system may employ continuity or mass conservation. For example, the MRI image processing and analysis system may determine if a flow into a bounded volume matches a flow out of the bounded volume.

In some implementations, the MRI image processing and analysis system may attempt to correct the phase aliasing, for instance by adding a corrective value (e.g., $2\pi$). Other approaches include a multi-VENC approach where a plurality of passes at a variety of VENC parameters (i.e., different frequencies) are tried to see which works the best. multiple Signal Unwrapping In some instances the appearance of certain portions of an image may appear in an incorrect location. For example, a lower or bottom portion of an image may appear at the top of the image or frame. This results form an incorrect ordering of data or information, which since the signal is periodic often results in incorrect rendering at the ends of the image (e.g., upper end, lower end). This time of error may be referred to as image wrapping or magnitude aliasing.

In such instances the MRI image processing and analysis system may implement a corrective action, for instance cropping the incorrectly located (e.g., aberrant) portion from the image or even correcting the image by moving the incorrectly located portion to the correct location within the image or image frame. In some implementations, the MRI image processing and analysis system can rely on user input to identify the incorrectly located portion. In other implementations, the MRI image processing and analysis system may autonomously identify the incorrectly located portion. For example, the MRI image processing and analysis system may analyze the image data for discontinuities. For instance, the MRI image processing and analysis system may compare are the image for temporal slice by temporal slice consistency. The MRI image processing and analysis system may, for instance, identify gradients or steps in voxel intensity values (magnitudes). For example, a large change in magnitude (e.g., doubling) in static tissue should not occur, thus such is detected as an error.

Other Artifacts

In some instances artifacts may appear in the MRI data set. For example, movement of a patient or portion thereof may give rise to a blurring of a resulting image. Also for example, presence of metal may give rise to streaks or other visual artifacts in the resulting image. Contrasts agents may also give rise to artifacts.

Typically these artifacts are difficult to correct. However, the MRI image processing and analysis system may detect the appearance of artifacts, and alert the medical care provider (e.g., physician) of the existence of artifacts in the data set.

Flow Driven Segmentation

The system may, for example automatically or autonomously, identify structures (e.g., 1D, 2D, 3D flow structures) in the 4D flow information, and may identify clinical makers. For example, the system may, automatically or autonomously, identify clinical makers such as anatomical and/or temporal clinical markers or clinical landmarks. Clinical makers may, for example, include one or more of aneurysms, stenosis, and plaque. Clinical markers may, for example, include anatomical markers or landmarks, such as various structures of the heart, for instance an apex of the heart, the aorta, the vena cava, and values such as the mitral valve or tricuspid valve. Clinical markers may, for example, include other known structures and/or other signatures. In some instances, the system may use the structures to identify various clinical markers. The system may, for example automatically or autonomously, segment or delineate various structures or clinical markers. For instance, the system may segment or delineate the lungs from other bodily tissue, for example based at least in part on the highly dynamic nature of the air in the lungs as compare to the relatively less dynamic nature of the other bodily tissue (e.g., cardiac tissue). Also for instance, the system may segment or delineate blood tissue from non-blood tissue, again based in part on the relatively dynamic and/or periodic nature of the blood tissue relative to the non-blood tissue, for example. Also for instance, the system may segment or delineate fluid substances (e.g., air in the lungs, blood in the vasculature or heart) from non-fluid tissue (e.g., vasculature, heart, fat).

Blood flow in a particular location in a body can frequently be characterized by a velocity of that blood flow over time. This is particularly true for blood flow within the heart and in the main arteries and veins of the body. Because of the rhythmic nature of the cardiac cycle, one method of characterizing blood flow patterns in a temporally resolved velocity data-set, where the time-points are distributed evenly over a single cardiac cycle, is by examining the components of a Discrete Fourier Transform (DFT) calculated at each voxel or pixel over the available time-points. Analysis can be performed via one or more processors using either transforms of the individual velocity components (x, y and z) or transforms of the resulting velocity magnitude.

The DFT components are useful for segmenting a blood pool from static tissue. For this purpose the low order, non-DC components are most useful as these components show strongly in both the blood flow within the heart and in the main arteries and veins connected to the heart, while any false velocity signals in static tissue, caused by eddy currents and other sources, tend to be largely static in time. Air within the lungs and outside of the body, with its typically high velocity signals, will also tend to show strongly in this transform, however these regions are easily removed using other techniques, for instance a simple threshold in images of the anatomy.

As different regions of blood flow (e.g., the aorta as compared to the inferior and superior vena cava) will have a different respective shapes or flow patterns, a general mask designed to locate all the blood flow within a chest scan can be obtained by combining the desired DFT components together without regard for their relative magnitude or phase. Application of such a mask will generally do a good job of separating the blood pool from static tissue. More refined masks designed to identify particular regions of the blood pool can be produced via the system by taking the phase and magnitude of the DFT components into account. The phase of the DFT components can be compared to the time-point of peak systole, with a probability assigned to each pixel based on the deviation of the phase from the expected value. The time-point of peak systole may be determined through various techniques described elsewhere. Likewise, the system may examine the relative magnitudes of the different DFT components and produce probability values based on the expected characteristics of the flow. The system may combine the probability values with the overall blood mask to produce highly accurate blood masks for the particular blood pool region of interest. In particular, the highly characteristic temporal nature of the blood flow in the aorta and pulmonary arteries can be easily distinguished and segmented from the rest of the blood pool using this technique.

Blood probability masks produced in this way for the arterial flow from the ventricles have the property, due to the strength by which they identify arterial flow, that a histogram of the resulting probability values can be used to automatically identify the appropriate probability cutoff value by the system, without assistance from a user (i.e., autonomously). Once an appropriate probability cutoff is determined for the arterial mask, the system may use the resulting mask to assist in determining probability cutoff values for other masks such as the aforementioned general blood mask. Due to the resulting accuracy of the arterial mask, it is also useful for providing points that can be guaranteed, with high probability, to be within the blood pool. Such points are useful to the system for various purposes, such as performing a flood fill of the less accurate general blood mask in order to clean it up by removing extraneous non-connected pieces.

Once the arterial flow mask is produced, marking regions of blood flow from the ventricles, the blood flow or blood pool can be automatically divided into aorta and pulmonary artery flow. Since there is no direct connection between the flow in the aorta and the flow in the pulmonary artery, the system can use flow directions and gradients and/or pathlines along with the probability values to separate the arterial mask into two main pieces. Once separated, the system can easily distinguish the aorta and pulmonary artery from each other by anatomical clues such as the average direction of flow or the relative positions of the two segments in space.

Since the tissue of the heart moves rhythmically with the cardiac cycle, calculating a per pixel DFT of a temporally resolved anatomy data set can be used to produce a probability mask for the wall of the heart, in a similar manor to that used for identifying blood pools in the temporally resolved velocity data-sets. As with this previous use, the non-zero low frequency components are the most useful for identifying motion having the same overall period as the heartbeat. Producing a mask that accurately identifies heart muscle is useful for a number of purposes. The system may combine the mask with the blood flow mask to produce a mask that covers the entire heart. This is useful, for example, in the described eddy current correction algorithms, where it is important to ignore regions of non-static tissue, or simply for segmenting the heart by the system for better visualization. A heart wall mask also provides useful information for segmenting the different regions of the blood pool and the chambers of the heart by the system, and can be used in combination with other metrics to assist with the automatic or autonomous identification of landmarks such as heart valves by the system.

A mask that accurately identifies heart muscle can also be used to provide metrics such as the location and size of the heart within the scan or image. The position of the heart within the scan or image has many uses. For example, the position can be used by blood flow segmentation routines executed by the system for determining whether blood is moving towards or away from the heart in order to separate, for example, right from left blood flow within the lungs.

The above described automated approaches remove the subjectivity in identifying anatomical structure and flow, which is endemic in conventional approaches, providing a high level or repeatability. This repeatability allows new uses for the MRI data. For example, MRI data for single patient may be reliably reviewed across different sessions for trends. Even more surprisingly, MRI data for a plurality of patients may be reliably reviewed for trends across a population or demographic.

The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 61/571,908, filed Jul. 7, 2011; International Patent Application No. PCT/US2012/045575, filed Jul. 5, 2012; and U.S. Provisional Patent Application No. 61/928,702, filed Jan. 17, 2014, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operation for use with magnetic resonance imaging (MRI) based medical imaging systems, the method comprising:
receiving a set of MRI data by at least one processor-based device, the set of MRI data comprising respective anatomical structure and blood flow information for each of a plurality of voxels;
identifying one or more instances of structure in the set of MRI flow data by at least one processor-based device, wherein identifying one or more instances of structure in the set of MRI flow data comprises identifying one or more instances of coherency in the set of MRI flow data; and
deriving contours in the set of MRI flow data based on the identified one or more instances of structure in the set of MRI flow data by at least one processor-based device.

2. The method of claim 1 wherein identifying one or more instances of coherency in the set of MRI flow data comprises identifying one or more instances of directional coherency in the set of MRI flow data.

3. The method of claim 1 wherein identifying one or more instances of coherency in the set of MRI flow data comprises identifying one or more instances of directional pathline or structural coherency in the set of MRI flow data.

4. The method of claim 1 wherein identifying one or more instances of coherency in the set of MRI flow data comprises identifying one or more instances of Discrete Fourier Transform (DFT) component coherency in the set of MRI flow data.

5. The method of claim 1 wherein identifying one or more instances of coherency in the set of MRI flow data comprises identifying one or more instances of acceleration coherency in the set of MRI flow data.

6. The method of claim 1, further comprising:
identifying one or more instances of clinical markers in the set of MRI flow data, by the at least one processor, based on the identified one or more instances of structure in the set of MRI flow data.

7. The method of claim 6 wherein identifying one or more instances of clinical markers in the set of MRI flow data comprises identifying one or more instances of anatomical markers and/or temporal markers in the set of MRI flow data.

8. The method of claim 6 wherein identifying one or more instances of clinical markers in the set of MRI flow data comprises identifying one or more instances of aneurysms, stenosis, or plaque in the set of MRI flow data.

9. The method of claim 6 wherein identifying one or more instances of clinical markers in the set of MRI flow data comprises identifying one or more pressure gradients in the set of MRI flow data.

10. The method of claim 6 wherein identifying one or more instances of clinical markers in the set of MRI flow data comprises identifying one or more instances of anatomical landmarks of a heart in the set of MRI flow data.

11. The method of claim 1 wherein deriving contours in the set of MRI flow data based on the identified one or more instances of structure in the set of MRI flow data comprises deriving contours in the set of MRI flow data that represent various bodily tissues.

12. The method of claim 11, further comprising:
autonomously segmenting blood bodily tissue from non-blood bodily tissues by at least one processor-based device; and
autonomously segmenting air from bodily tissues by at least one processor-based device.

13. The method of claim 1, further comprising:
applying a Discrete Fourier Transform (DFT) to each of a plurality of voxels in the set of MRI data over a plurality of available time-points, by the at least one processor-based device; and
examining a number of components of the DFT at each of the voxels over the available time-points by the at least one processor-based device.

14. The method of claim 13 wherein applying a DFT to each of a plurality of voxels in the set of MRI data over a plurality of available time-points comprises applying a DFT to three velocity components (x, y, z) of the blood flow information.

15. The method of claim 13 wherein applying a DFT to each of a plurality of voxels in the set of MRI data over a plurality of available time-points comprises applying a DFT to a resulting velocity magnitude of the blood flow information.

16. The method of claim 13, further comprising:
segmenting a blood pool from static tissue based at least part on the DFT components, by the at least one processor, wherein segmenting a blood pool from static tissue based at least part on the DFT components comprises segmenting the blood pool from the static tissue based at least part on a set of low order, non-DC DFT components, autonomously by the at least one processor.

17. The method of claim 13, further comprising:
combining a number of DFT components together without regard for relative magnitude or phase to produce a general mask to locate all blood flow within a chest scan, by the at least one processor.

18. The method of claim 13, further comprising:
combining a number of DFT components together taking into account relative magnitude or phase of the DFT components to produce a refined mask to identify a particular region of a blood pool in the body, by the at least one processor.

19. The method of claim 18, further comprising:
comparing a phase of the DFT components to a time-point of peak systole, and assigning a probability to each voxel based on an amount of deviation of the phase from an expected value, by the at least one processor.

20. The method of claim 19, further comprising:
distinguishing between a blood flow in the aorta and a blood flow in the pulmonary arteries based at least in part on the refined mask, by the at least one processor.

21. The method of claim 19, further comprising:
identifying a probability cutoff value based at least in part on a histogram of the resulting probability values, autonomously by the at least one processor.

22. The method of claim 19, further comprising:
identifying a probability cutoff value for an arterial specific mask based at least in part on a histogram of the resulting probability values, autonomously by the at least one processor; and
determining a probability cutoff values for at least one other mask based at least in part on the arterial specific mask, wherein determining a probability cutoff values for at least one other mask based at least in part on the arterial specific mask comprises performing a flood fill of a general blood mask to remove extraneous non-connected pieces.

23. The method of claim 22, further comprising:
separating the arterial specific mask into two main portions based at least in part on a number of flow directions and a number or gradients and/or a number of path-lines along with the resulting probability values, by the at least one processor.

24. The method of claim 23, further comprising:
distinguishing the aorta and the pulmonary artery from one another based at least in part at least one of an average direction of flow or a relative position of the two main portions in space, by the at least one processor.

25. The method of claim 19, further comprising:
producing a probability mask for a wall of the heart, autonomously by the at least one processor.

26. The method of claim 25, further comprising:
combining the probability mask for the wall of the heart with a blood flow mask, by the at least one processor.

27. The method of claim 25, further comprising:
employing the probability mask for the wall of the heart in performing eddy current correction, by the at least one processor.

28. The method of claim 25, further comprising:
employing the probability mask for the wall of the heart to provide at least one of a location and/or a size of the heart in an image, by the at least one processor.

29. A processor-based device, comprising:
at least one processor; and
at least one nontransitory processor-readable medium communicatively coupled to the at least one processor, and which stores at least one of processor-executable instructions or date which when executed causes the at least one processor to:
receive a set of MRI data by at least one processor-based device, the set of MRI data comprising respective anatomical structure and blood flow information for each of a plurality of voxels;
identify one or more instances of structure in the set of MRI flow data by at least one processor-based device, wherein identifying one or more instances of structure in the set of MRI flow data comprises identifying one or more instances of coherency in the set of MRI flow data; and
derive contours in the set of MRI flow data based on the identified one or more instances of structure in the set of MRI flow data by at least one processor-based device.

30. The processor-based device of claim 29 wherein the at least one of processor-executable instructions or date, when executed, causes the at least one processor to identify one or more instances of directional coherency in the set of MRI flow data.

31. The processor-based device of claim 29 wherein the at least one of processor-executable instructions or date, when executed, causes the at least one processor to identify one or more instances of directional pathline or structural coherency in the set of MRI flow data.

32. The processor-based device of claim 29 wherein the at least one of processor-executable instructions or date, when executed, causes the at least one processor to identify one or more instances of Discrete Fourier Transform (DFT) component coherency in the set of MRI flow data.

33. The processor-based device of claim 29 wherein the at least one of processor-executable instructions or date, when executed, causes the at least one processor to identifying one or more instances of acceleration coherency in the set of MRI flow data.

34. The processor-based device of claim 29 wherein the at least one of processor-executable instructions or date, when executed, causes the at least one processor further to identify one or more instances of clinical markers in the set of MRI flow data, by the at least one processor, based on the identified one or more instances of structure in the set of MRI flow data.

35. The processor-based device of claim 34 wherein the at least one of processor-executable instructions or date, when executed, causes the at least one processor to identify one or more instances of anatomical markers and/or temporal markers in the set of MRI flow data in order to identify one or more instances of clinical markers in the set of MRI flow data.

36. The processor-based device of claim 34 wherein the at least one of processor-executable instructions or date, when executed, causes the at least one processor to identify one or more instances of aneurysms, stenosis, or plaque in the set of MRI flow data in order to identify one or more instances of clinical markers in the set of MRI flow data.

37. The processor-based device of claim 34 wherein the at least one of processor-executable instructions or date, when executed, causes the at least one processor to identify one or more pressure gradients in the set of MRI flow data in order to identify one or more instances of clinical markers in the set of MRI flow data.

38. The processor-based device of claim 34 wherein the at least one of processor-executable instructions or date, when executed, causes the at least one processor to identify one or more instances of anatomical landmarks of a heart in the set of MRI flow data identify one or more instances of clinical markers in the set of MRI flow data.

39. The processor-based device of claim 29 wherein the at least one of processor-executable instructions or date, when executed, causes the at least one processor to derive contours in the set of MRI flow data that represent various bodily tissues in order to derive contours in the set of MRI flow data based on the identified one or more instances of structure in the set of MRI flow data.

40. The processor-based device of claim 29 wherein the at least one of processor-executable instructions or date, when executed, causes the at least one processor further to:
autonomously segment blood bodily tissue from non-blood bodily tissues by at least one processor-based device; and
autonomously segment air from bodily tissues by at least one processor-based device.

* * * * *